(12) United States Patent
Arini et al.

(10) Patent No.: US 7,978,885 B2
(45) Date of Patent: Jul. 12, 2011

(54) ANALYSING BIOLOGICAL ENTITIES

(75) Inventors: Nicholas S. Arini, Southampton (GB); Ian D. Goodyer, Eastbourne (GB); Dietrich O. Ruehlmann, Gaithersburg, MD (US); Nicholas Thomas, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 1181 days.

(21) Appl. No.: 10/561,574

(22) PCT Filed: Jul. 28, 2004

(86) PCT No.: PCT/GB2004/003247
§ 371 (c)(1), (2), (4) Date: Jan. 26, 2007

(87) PCT Pub. No.: WO2005/012880
PCT Pub. Date: Feb. 10, 2005

(65) Prior Publication Data
US 2007/0160270 A1    Jul. 12, 2007

(30) Foreign Application Priority Data
Jul. 29, 2003 (GB) .................................. 0317679.9

(51) Int. Cl.
*G06K 9/00* (2006.01)
(52) U.S. Cl. ........ 382/128; 382/131; 382/132; 382/133; 250/303; 250/583
(58) Field of Classification Search ............ 436/57; 382/128, 131, 129, 133, 130, 134; 348/371; 356/417; 250/582, 584
See application file for complete search history.

(56) References Cited

U.S. PATENT DOCUMENTS

| | | | | |
|---|---|---|---|---|
| 4,389,670 A | * | 6/1983 | Davidson et al. | 348/162 |
| 5,031,099 A | | 7/1991 | Kettler | |
| 5,347,139 A | * | 9/1994 | Barker et al. | 250/583 |

(Continued)

FOREIGN PATENT DOCUMENTS
DE    100 65 632    11/2001
(Continued)

OTHER PUBLICATIONS

Demongeot, J., et al., "A Differential Geometry Approach for Biomedical Image Processing", *Comptes Rendus—Biologies*, Elsevier, Paris, France, vol. 325, No. 4, 2002, p. 367-374.

*Primary Examiner* — Vikkram Bali
*Assistant Examiner* — Nancy Bitar
(74) *Attorney, Agent, or Firm* — Yonggang Ji

(57) ABSTRACT

A method of analysing a plurality of biological entities using an imaging apparatus. The method comprises: providing a marker for said plurality of biological entities, said marker being capable of identifying objects within said plurality of biological entities when detected using the imaging apparatus, the method of provision being arranged such that said marker is capable of identifying said objects during a first time period, and said marker is less capable of identifying said objects during a second time period; during the first time period, recording a marked-up image in which spatial definitions of said objects are identifiable from said marker; during the second time period, recording a first image of said plurality of biological entities; and generating a spatial definition for an object in said first image using data derived from said marked-up image.

31 Claims, 10 Drawing Sheets

| U.S. PATENT DOCUMENTS | | | |
|---|---|---|---|
| 6,103,479 A | 8/2000 | Taylor | |
| 6,613,210 B1 * | 9/2003 | Hassard et al. | 204/461 |
| 6,717,174 B2 * | 4/2004 | Karellas | 250/582 |
| 6,986,993 B1 | 1/2006 | Ghosh et al. | |
| 7,467,117 B2 * | 12/2008 | Kermani | 706/20 |
| 7,567,293 B2 * | 7/2009 | Perlman et al. | 348/371 |

| FOREIGN PATENT DOCUMENTS | | |
|---|---|---|
| EP | 0401077 * | 5/1990 |
| EP | 0 401 077 | 12/1990 |
| JP | 59-126529 | 7/1984 |
| WO | WO 97/45730 | 12/1997 |
| WO | WO 00/03246 | 1/2000 |

* cited by examiner

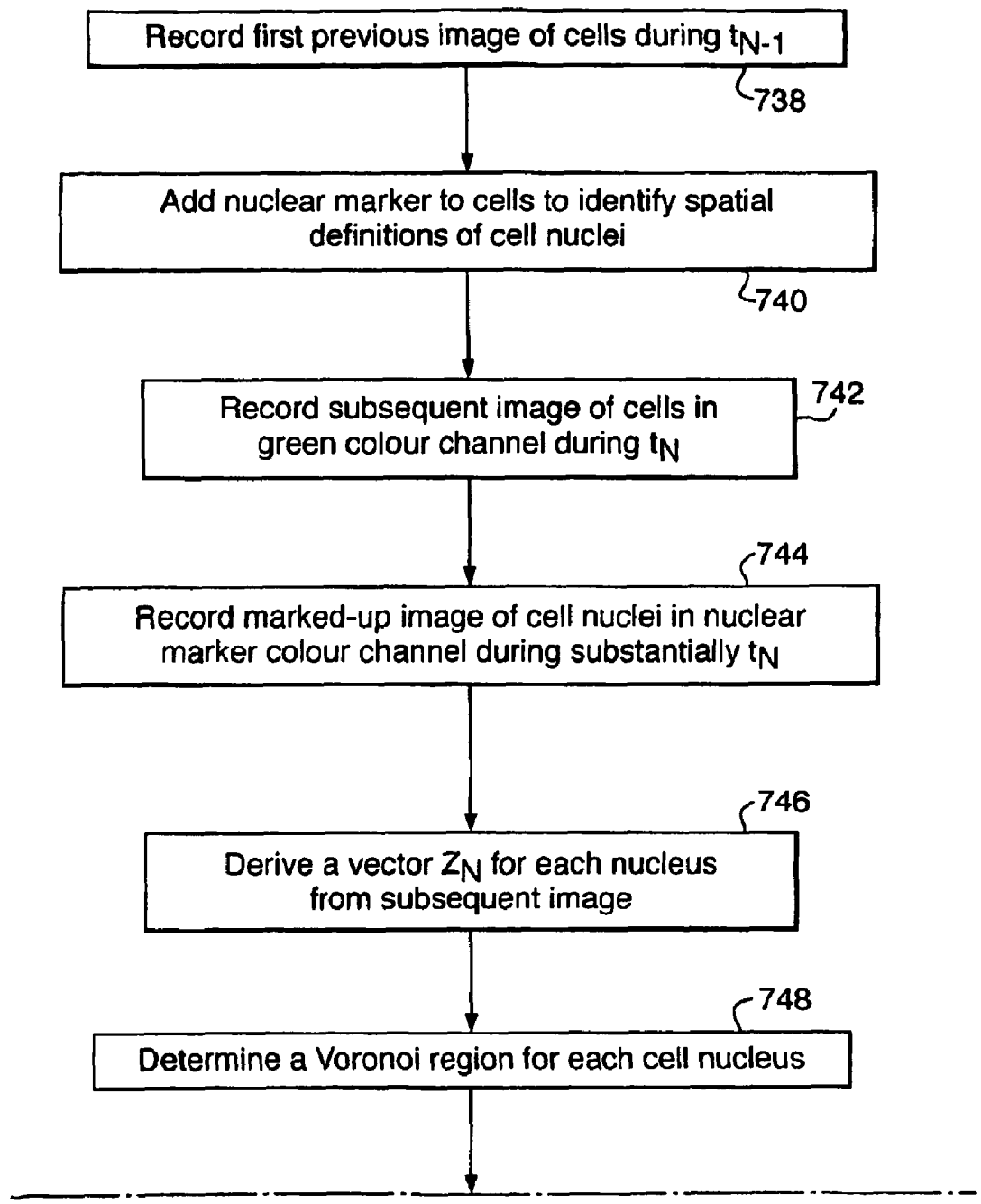

ANALYSING BIOLOGICAL ENTITIES

CROSS REFERENCE TO RELATED APPLICATIONS

This application is a filing under 35 U.S.C. §371 and claims priority to international patent application number PCT/GB2004/003247 filed Jul. 28, 2004, published on Feb. 10, 2005 as WO2005/012880 and also claims priority to patent application number 0317679.9 filed in the Great Britain Patent Office on Jul. 29, 2003; the disclosures of which are incorporated herein by reference in their entireties.

FIELD OF THE INVENTION

The present invention relates to a method of analysing biological entities, in particular but not exclusively biological cells. The invention further relates to computer software and apparatus adapted to carry out such a method.

BACKGROUND OF THE INVENTION

Currently in drug discovery and development and in general biological research, methods and apparatus for accurately performing cell-based assays are used. Cell-based assays are advantageously employed for assessing the biological activity of chemical compounds.

In assessing the biological activity of chemical compounds, there is a need to quickly and inexpensively screen large numbers of chemical compounds. This need has arisen in the pharmaceutical industry where it is necessary to test chemical compounds for activity against a variety of biochemical targets, for example, receptors, enzymes and nucleic acids. These chemical compounds are collected in large libraries, sometimes exceeding one million distinct compounds. The use of the term chemical compound is intended herein to be interpreted broadly so as to include, but not to be limited to, simple organic and inorganic molecules, proteins, peptides, nucleic acids and oligonucleotides, carbohydrates, lipids, or any chemical structure of biological interest.

In the field of chemical compound screening, cell-based assays are run on populations of cells.

International patent application WO 99/47963 describes a translocation assay in which two or more cell species, for example a biological cell nucleus and a biological cell transcription factor protein, are fluorescently labelled. In the assay, images are acquired including both the nucleus and the transcription factor species. The images are processed such that a co-localisation of the two species may be determined in order to analyse a migration of the transcription factor within the cell. For the course of time of the translocation assay, the cell nucleus is fluorescently labelled with a nuclear dye.

International patent application WO 03/031612 describes a process for determining a phase of a biological cell cycle by analysing nucleic acid, for example DNA, of cell nuclei of the cells as a function of time. Images of the cells are recorded over the course of the assay and, in order to analyse the cell nuclei using these images, the nuclei are stained using a nuclear dye The staining of cellular nucleic acids, for example DNA, with a nuclear dye such as Hoechst (propidium iodide) or DRAQ5, is used to identify a spatial definition of a cell nucleus, from which to form a nuclear mask. The properties of the cell may be determined by measuring characteristics of the cell inside and outside the nuclear mask area. However, the nuclear dye is destructive to the structure of the nucleic acid and hence multiple samples of cells are required to study the progression of biological activity over time. In the case where many hundreds of samples are to be analysed, this deterioration of the nucleic acid can become rate limiting.

The constituent molecules of such nuclear dyes bind to the molecule of the nucleic acid molecule by intercalating between the base pairs of the nucleic acid. This intercalation, however, over the course of an experiment having an extended time period proves to be toxic to the nucleic acid. The toxicity results in damage to the structure of the nucleic acid leading to mutations in the genetic code. These mutations interfere with the correct functioning of the cell and in the case of screening chemical compounds for their effects on biological cell systems, introduces undesired errors into results data being collected.

It is an object of the present invention to address the problems in the prior art relating to the use of a marker such as a nuclear dye.

SUMMARY OF THE INVENTION

According to a first aspect of the invention there is provided a method of analysing a plurality of biological entities using an imaging apparatus, the method comprising:

a) providing a marker for said plurality of biological entities, said marker being capable of identifying objects within said plurality of biological entities when detected using the imaging apparatus, the method of provision being arranged such that said marker is capable of identifying said objects during a first time period, and said marker is less capable of identifying said objects during a second time period;

b) during the first time period, recording a marked-up image in which spatial definitions of said objects are identifiable from said marker;

c) during the second time period, recording a first image of said plurality of biological entities; and d) generating a spatial definition for an object in said first image using data derived from said marked-up image.

Preferably the first time period is previous to said second time period, or preferably the first time period is subsequent to said second time period.

Preferably, the biological entities are biological cells.

Preferably, the objects comprise biological cell nuclei.

Preferably, the method further comprises analysing characteristics of the plurality of biological entities by analysing the first image using the generated spatial definition.

With the marker provided for the plurality of biological cells being capable of identifying spatial definitions of the cell nuclei in the marked-up image, a spatial definition may be generated for a cell nucleus in the first image in which the marker is less capable of identifying the cell nuclei. Therefore, with the first image being recorded during the second time period which is previous to, or subsequent to, the first time period during which the marked-up image is recorded, it is not necessary to have the marker present in the biological cells during any time period other than the first time period. Consequently it is possible to analyse characteristics of the plurality of cells and obtain results data of a more accurate and reliable nature for screening analyses of for example, chemical compounds, over an extended time period.

In a second aspect of the invention there is provided a method of image analysis for analysing a plurality of biological entities from images produced using an imaging apparatus, the method comprising:

a) obtaining a marked-up image of said plurality of biological entities, said marked-up image having been recorded during a first time period in which a marker provided for said plurality of biological entities is capable of identifying objects within said plurality of entities;

b) obtaining a first image of said plurality of biological entities, said first image having been recorded during a second time period in which said marker is less capable of identifying said objects; and c) generating a spatial definition of an object for said first image using data derived from said marked-up image.

This aspect of the invention relates specifically to a method of image analysis, which may be conducted at a different time, and/or location, to that of recording of the images.

Further features and advantages of the invention will become apparent from the following description of preferred embodiments of the invention, given by way of example only, which is made with reference to the accompanying drawings.

DETAILED DESCRIPTION OF THE INVENTION

The present invention is useful for identifying pharmacological agents for the treatment of disease. It provides a high throughput method for conducting a wide variety of biological assays where one or more luminescent markers are employed to measure a biological response. Such assays can be conducted on chemical compounds or any molecule of biological interest, included but not limited to drug candidates, such as those found in combinatorial libraries, thus allowing the high throughput screening of such chemical compounds.

The techniques of the present invention may be used in assays in which data are acquired on a plurality of biological entities for example individual biological cells, on a cellular or sub-cellular level, sufficiently rapidly so as to permit the acquisition of such data on a sufficient number of cells to constitute a statistically meaningful sample of the cell population.

These assays may make use of various different markers, including known fluorophores or fluorescent labels including but not limited to fluorescein, rhodamine, Texas Red, Amersham Corp. stains Cy3, Cy5, Cy5.5 and Cy7, Hoechst's nuclear stains and Coumarin stains (see Haugland R. P. Handbook of Fluorescent Probes and Research Chemicals $6^{th}$ Ed., 1996, Molecular Probes, Inc., Eugene, Oreg.)

Optical Configuration

Figure 1:
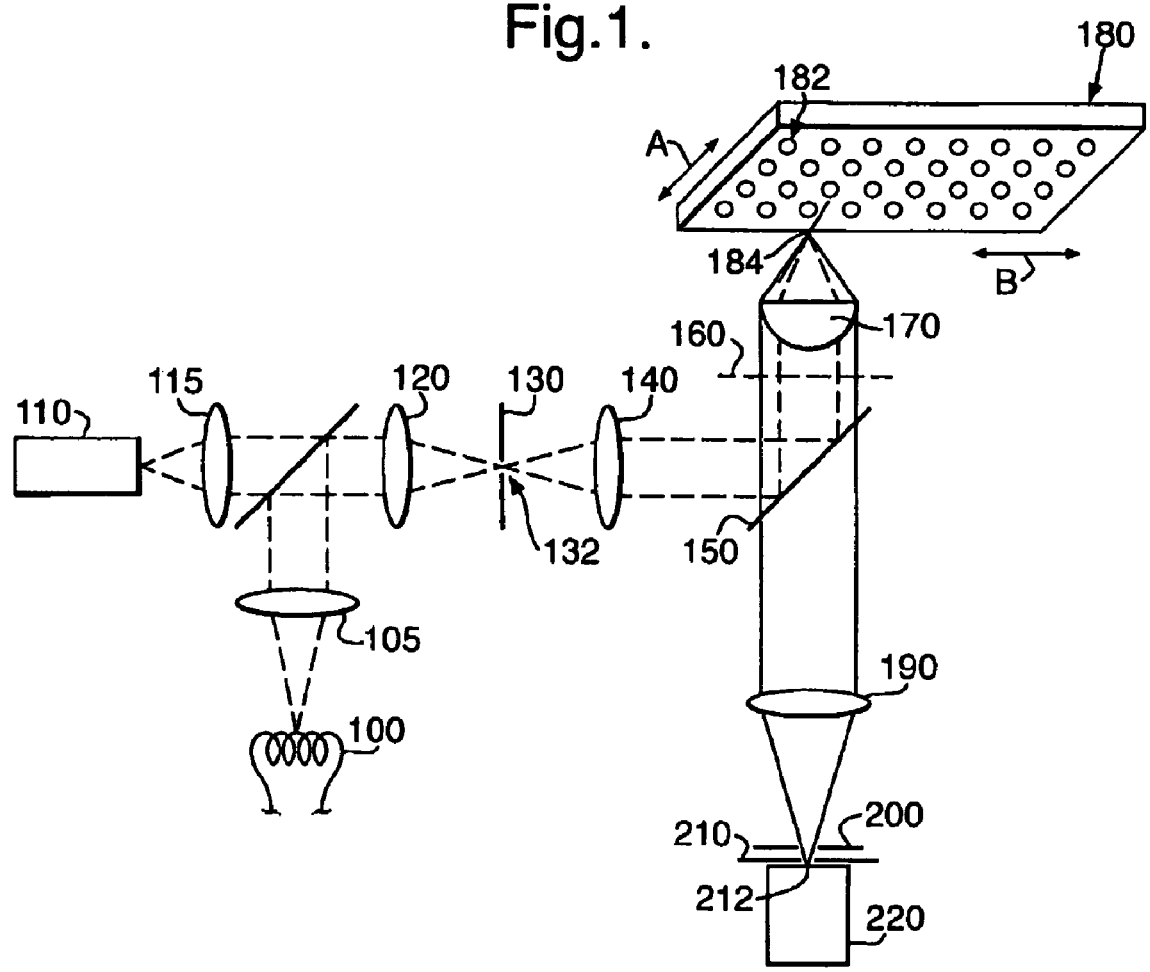
FIG. 1 is a schematic view of a line-scan confocal microscope used to image a plurality of biological entities.

FIG. 1 shows imaging apparatus comprising a line-scan confocal microscope of an embodiment of the present invention. The microscope comprises a source 100 or 110 of electromagnetic radiation for example, in the optical range, 350-750 nm, a cylindrical lens 120, a first slit mask 130, a first relay lens 140, a dichroic mirror 150, an objective lens 170, a microtiter plate 180 containing a two-dimensional array of sample wells 182, a tube lens 190, a filter 200, a second slit mask 210 and a detector 220. These elements are arranged along optical axis OA with slit apertures 132, 212 in masks 130, 210 extending perpendicular to the plane of FIG. 1. The focal lengths of lenses 140, 170 and 190 and the spacings between these lenses as well as the spacings between mask 130 and lens 140, between objective lens 170 and microtiter plate 180 and between lens 190 and mask 210 are such as to provide a confocal microscope. In this embodiment, electromagnetic radiation from a lamp 100 or a laser 110 is focused to a line using a cylindrical lens 120. The shape of the line is optimized by a first slit mask 130. The slit mask 130 is depicted in an image plane of the optical system, that is in a plane conjugate to the object plane. The illumination stripe formed by the aperture 132 in the slit mask 130 is relayed by lens 140, dichroic mirror 150 and objective lens 170 onto a microtiter plate 180 which contains a two-dimensional array of sample wells 182. For convenience of illustration, the optical elements of FIG. 1 are depicted in cross-section and the well plate in perspective. The projection of the line of illumination onto well plate 180 is depicted by line 184 and is also understood to be perpendicular to the plane of FIG. 1. As indicated by arrows A and B, well plate 180 may be moved in two dimensions (X, Y) parallel to the dimensions of the array by means not shown.

In an alternative embodiment, the slit mask 130 resides in a Fourier plane of the optical system, that is in a plane conjugate to the objective back focal plane (BFP) 160. In this case the aperture 132 lies in the plane of the figure, the lens 140 relays the illumination stripe formed by the aperture 132 onto the back focal plane 160 of the objective 170 which transforms it into a line 184 in the object plane perpendicular to the plane of FIG. 1.

In an additional alternative embodiment the slit mask 130 is removed entirely. According to this embodiment, the illumination source is the laser 110, the light from which is focused into the back focal plane 160 of the objective 170. This can be accomplished by the combination of the cylindrical lens 120 and the spherical lens 140 as shown in FIG. 1, or the illumination can be focused directly into the plane 160 by the cylindrical lens 120.

An image of the sample area, for example a sample of a plurality of biological cells in a sample well 182, is obtained by projecting the line of illumination onto a plane within the sample, imaging the fluorescence emission therefrom onto a detector 220 and moving the plate 180 in a direction perpendicular to the line of illumination, synchronously with the reading of the detector 220. In the embodiment depicted in FIG. 1, the fluorescence emission is collected by the objective lens 170, projected through the dichroic beamsplitter 150, and imaged by lens 190 through filters 200 and a second slit mask 210 onto a detector 220, such as is appropriate to a confocal imaging system having an infinity-corrected objective lens 170. The dichroic beamsplitter 150 and filter 200 preferentially block light at the illumination wavelength. The detector 220 illustratively is a camera and may be either one dimensional or two dimensional. If a one dimensional detector is used, slit mask 210 is not needed. The illumination, detection and translation procedures are continued until the prescribed area has been imaged. Mechanical motion is simplified if the sample is translated at a continuous rate. Continuous motion is most useful if the camera read-time is small compared to the exposure-time. In a preferred embodiment, the camera is read continuously. The displacement d of the sample during the combined exposure-time and read-time may be greater than or less than the width of the illumination line W, exemplarily $0.5\ W \leq d \leq 5\ W$. All of the wells of a multiwell plate can be imaged in a similar manner.

Alternatively, the microscope can be configured to focus a line of illumination across a number of adjacent wells, limited primarily by the field-of-view of the optical system. Finally, more than one microscope can be used simultaneously.

The size and shape of the illumination stripe 184 is determined by the width and length of the Fourier transform stripe in the objective lens back focal plane 160. For example, the length of the line 184 is determined by the width of the line in 160 and conversely the width in 184 is determined by the length in 160. For diffraction-limited performance, the length of the illumination stripe at 160 is chosen to overfill the objective back aperture. It will be evident to one skilled in the art that the size and shape of the illumination stripe 184 can be controlled by the combination of the focal length of the cylindrical lens 120 and the beam size at 120, that is by the effective numerical aperture in each dimension, within the restrictions imposed by aberrations in the objective, and the objective field of view.

The dimensions of the line of illumination 184 are chosen to optimize the signal to noise ratio. Consequently, they are sample dependent. Depending on the assay, the resolution may be varied between diffraction-limited, i.e., less than 0.5 µm, and approximately 5 µm. The beam length is preferably determined by the objective field of view, exemplarily between 0.5 and 1.5 mm. A Nikon ELWD, 0.6 NA, 10× objective, for example, has a field of view of approximately 0.75 mm. The diffraction-limited resolution for 633 nm radiation with this objective is approximately 0.6 µm or approximately 1100 resolution elements.

The effective depth resolution is determined principally by the width of aperture 212 in slit mask 210 or the width of the one dimensional detector and the image magnification created by the combination of the objective lens 170 and lens 190. The best depth resolution of a confocal microscope approaches 1 µm. In the present application, a depth resolution of 5-10 µm may be sufficient or even advantageous.

For example, when the sample of interest, such as a live cell, contains insufficient fluorophores in a diffraction-limited volume to permit an adequate signal-to-noise image in a sufficiently brief image-acquisition time, it is advantageous to illuminate and collect the emission from a larger than diffraction-limited volume. A similar situation prevails in the case of video-rate kinetics studies of transient events such as ion-channel openings. Practically, this is accomplished by underfilling the back aperture of the objective lens, which is equivalent to increasing the diameter of the illumination aperture. The effective numerical aperture ("NA") of the illumination is less than the NA of the objective. The fluorescence emission is, however, collected with the full NA of the objective lens. The width of aperture 212 must be increased so as to detect emission from the larger illumination volume. At an aperture width a few times larger than the diffraction limit, geometrical optics provides an adequate approximation for the size of the detection-volume element:

Lateral Width: $a_d = d_d/M$,

Axial Width: $Z_d = \sqrt{2} a_d / \tan \alpha$, where M is the magnification, $d_d$ is the width of aperture 212 and α is the half-angle subtended by the objective 170. It is an important part of the present invention that the illumination aperture 132 or its equivalent in the embodiment having no aperture and the detection aperture 212 be independently controllable.

Multi-Wavelength Configuration

A different embodiment using imaging apparatus enabling multi-wavelength fluorescence imaging is preferred for certain types of assays. In this way, image data can be generated for the same area being imaged in a plurality of different colour channels simultaneously.

Figure 2A:
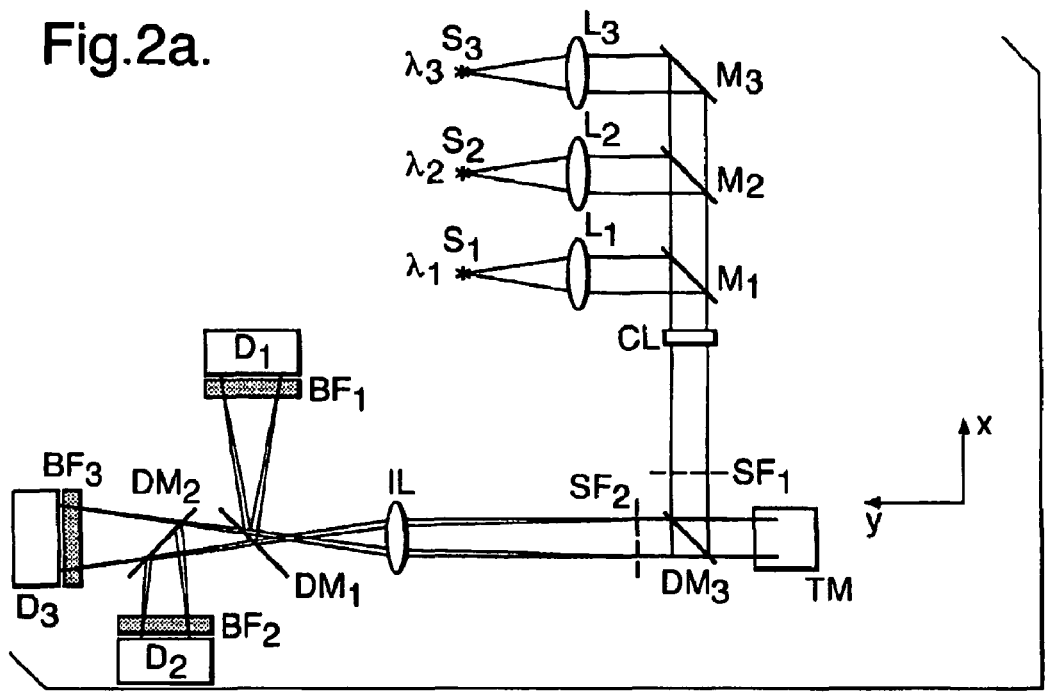
FIGS. 2a and 2b schematically show respectively a top view and a side view of a multi-wavelength line-scan confocal microscope used to image a plurality of biological entities in accordance with embodiments of the present invention.
Figure 2B:
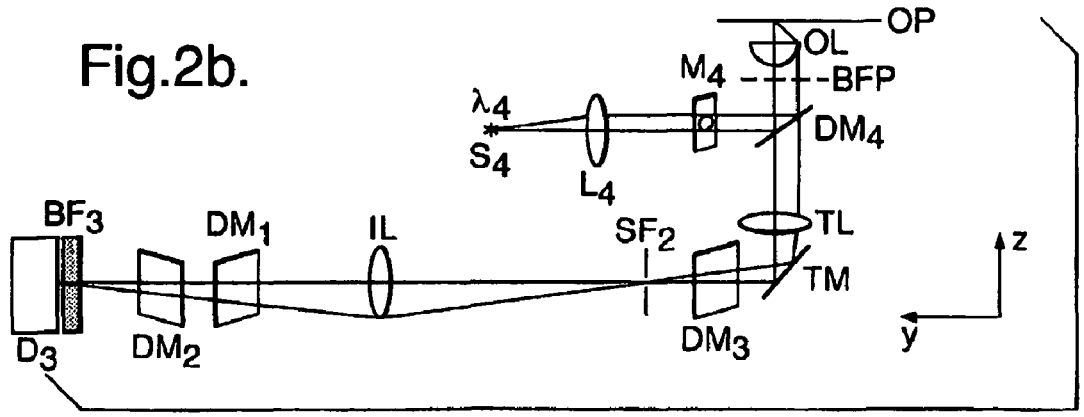

The number of independent wavelengths or colour channels will depend on the specific assay being performed. In one embodiment three illumination wavelengths are used. FIGS. 2A and 2B depict the ray paths in a three-colour line-scan confocal imaging system, from a top view and a side view respectively. In general, the system comprises several sources $S_n$ of electromagnetic radiation, collimating lenses $L_n$, and mirrors $M_n$ for producing a collimated beam that is focused by cylindrical lines CL into an elongated beam at first spatial filter $SF_1$, a confocal microscope between first spatial filter $SF_1$, and second spatial filter $SF_2$ and an imaging lens IL, beamsplitters $DM_1$ and $DM_2$ and detectors $D_n$ for separating and detecting the different wavelength components of fluorescent radiation from the sample. Spatial filters SF, and $SF_1$, and $SF_2$ preferably are slit masks.

In particular, FIG. 2A depicts sources, $S_1$, $S_2$ and $S_3$, for colour channels $\lambda_1$, $\lambda_2$ and $\lambda_3$, and lenses $L_1$, $L_2$ and $L_3$ that collimate the light from the respective sources. Lenses $L_1$, $L_2$ and $L_3$, preferably are adjusted to compensate for any chromaticity of the other lenses in the system. Mirrors $M_1$, $M_2$ and $M_3$ are used to combine the illumination colour channels from sources $S_n$. The mirrors $M_2$ and $M_1$ are partially transmitting, partially reflecting and preferentially dichroic. $M_2$, for example, should preferentially transmit $\lambda_3$, and preferentially reflect $\lambda_2$. It is thus preferential that $\lambda_3$ be greater than $\lambda_2$.

Operation of the microscope in a confocal mode requires that the combined excitation beams from sources $S_n$ be focused to a "line", or an highly eccentric ellipse, in the object plane OP. As discussed in connection to FIG. 1 above, a variety of configurations may be used to accomplish this. In the embodiment depicted in FIG. 2, the combined illumination beams are focused by cylindrical lens CL into an elongated ellipse that is coincident with the slit in the spatial filter $SF_1$. As drawn in FIGS. 2A and 2B, the slit mask $SF_1$ resides in an image plane of the system, aligned perpendicular to the propagation of the illumination light and with its long axis in the plane of the page of FIG. 2A. The lenses TL and OL relay the illumination line from the plane containing SF, to the object plane OP. A turning mirror, TM, is for convenience. In another embodiment, $DM_3$ is between TL and OL and CL focuses the illumination light directly into the BFP. Other embodiments will be evident to one skilled in the art.

Referring to FIG. 2B, the light emitted by the sample and collected by the objective lens, OL, is imaged by the tube lens, TL, onto the spatial filter, $SF_2$. $SF_2$ is preferentially a slit aligned so as to extend perpendicular to the plane of the page. Thus, the light passed by filter $SF_2$ is substantially a line of illumination. $SF_2$ may be placed in the primary image plane or any plane conjugate thereto. $DM_3$ is partially reflecting, partially transmitting and preferably "multichroic". Multi-wavelength "dichroic" mirrors, or "multichroic" mirrors can be obtained that preferentially reflect certain wavelength bands and preferentially transmit others.

Here, $\delta\lambda_1$, will be defined to be the fluorescence emission excited by $\lambda_1$. This will, in general, be a distribution of wavelengths somewhat longer than $\lambda_1$. $\delta\lambda_2$ and $\delta\lambda_3$ are defined analogously. $DM_3$ preferentially reflects $\lambda_n$, and preferentially transmits $\delta\lambda_n$, n=1, 2, 3. The light transmitted by $SF_2$ is imaged onto the detection devices, which reside in planes conjugate to the primary image plane. In FIG. 2A, an image of the spatial filter $SF_2$ is created by lens IL on all three detectors, $D_n$. This embodiment is preferred in applications requiring near-perfect registry between the images generated by the respective detectors. In another embodiment, individual lenses $IL_n$ are associated with the detection devices, the lens pairs IL and $IL_n$ serving to relay the image of the spatial filter $SF_2$ onto the respective detectors $D_n$. The light is split among the detectors by mirrors $DM_1$ and $DM_2$. The mirrors are partially transmitting, partially reflecting, and preferentially dichroic. $DM_1$ preferentially reflects $\delta\lambda_1$ and preferentially transmits $\delta\lambda_2$ and $\delta\lambda_3$. The blocking filter, $\delta\lambda_1$, preferentially transmits $\delta\lambda_1$ effectively blocking all other wavelengths present. $DM_2$ preferentially reflects $\delta\lambda_2$ and preferentially transmits $\delta\lambda_3$. The blocking filters, $BF_2$ and $BF_3$, preferentially transmit $\delta\lambda_2$ and $\delta\lambda_3$ respectively, effectively blocking all other wavelengths present.

Scanning Mirror Configuration

In some embodiments of this invention, rapid data acquisition is provided by framing images at video rates. Video-rate imaging allows up to 30 or even 60 frames per second. In the present use, it is intended to connote frame rates with an order-of-magnitude of 30 Hz. In a preferred embodiment, video-rate imaging is achieved by illuminating along one dimension of the sample plane and scanning the illumination beam in the direction perpendicular thereto so as to effect a relative translation of the illumination and sample. The scanning stage is generally massive. Consequently, it cannot be moved sufficiently rapidly.

Figure 3A:
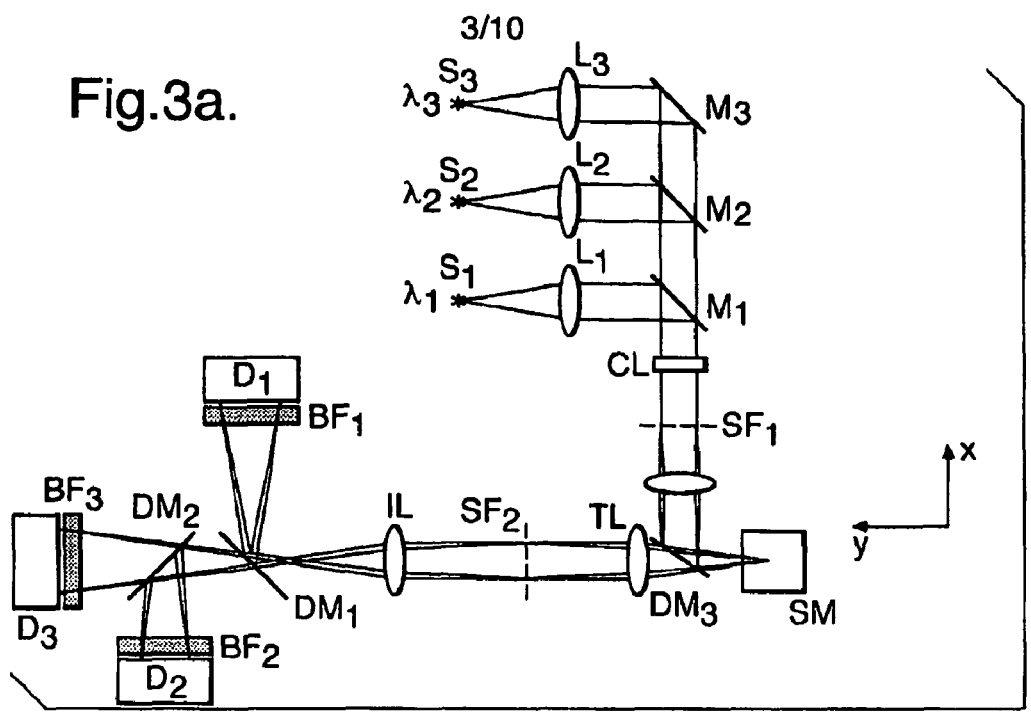
FIGS. 3a and 3b show respectively a top view and a side view of a ray path of the multi-wavelength line-scan confocal microscope with a scanning mirror according to an embodiment of the present invention.
Figure 3B:
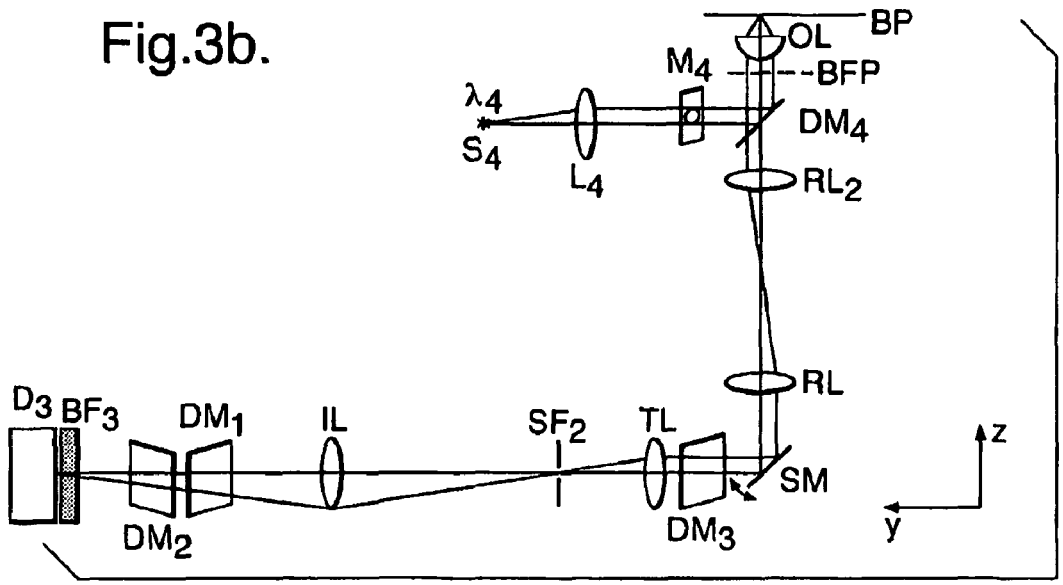

FIG. 3 depicts an embodiment of the invention utilizing a scanning mirror, SM. The mirror is advantageously placed in a plane conjugate to the objective back focal plane (BFP): A rotation in the BFP (or a plane conjugate thereto) effects a translation in the object plane (OP) and its conjugate planes. The full scan range of SM need only be a few degrees for typical values of the focal lengths of the lenses $RL_1$ and $RL_2$. As shown in FIG. 3, this lens pair images the BFP onto the SM at a magnification of one, but a variety of magnifications can be advantageously used. The limiting factors to the image acquisition rate are the camera read-rate and the signal strength. In the imaging mode described above, data can be acquired continuously at the camera read-rate, exemplarily 1 MHz. With a scanning mirror, it is preferable to acquire data uni-directionally. The idealized scanning motion allowing one to acquire data continuously is the sawtooth. In practice, the combination of turn-around and return scan times will constitute ~⅓-⅔ of the scan period. Assuming 50% dead-time, a mirror oscillation frequency of 50 Hz and a pixel acquisition rate of 1 MHz, ~10,000 pixels would be acquired per frame at 50 frames per second, which is sufficient to define and track individual objects, such as cells, from frame to frame. $10^4$ pixels per image is, however, $10^2$-times fewer than was generally considered above. Depending on the application, it is advantageous to acquire relatively smaller images at high resolution, e.g. 50-μm×50-μm at 0.5-μm×0.5-μm pixelation, or relatively larger images at lower resolution, e.g. 200-μm×200-μm at 2-μm pixelation.

Autofocus

In preferred embodiments of the present invention, the sample lies in the object plane of an imaging system. Accordingly, an autofocus mechanism is used that maintains the portion of the sample in the field-of-view of the imaging system within the object plane of that system. The precision of planarity is determined by the depth-of-field of the system. In a preferred embodiment, the depth-of-field is approximately 10 μm and the field-of-view is approximately 1 $mm^2$.

The autofocus system operates with negligible delay, that is, the response time is short relative to the image acquisition-time, exemplarily 0.01-0.1 s. In addition, the autofocus light source is independent of the illumination light sources and the sample properties. Among other advantages, this configuration permits the position of the sample carrier along the optical axis of the imaging system to be determined independent of the position of the object plane.

Figure 2C:
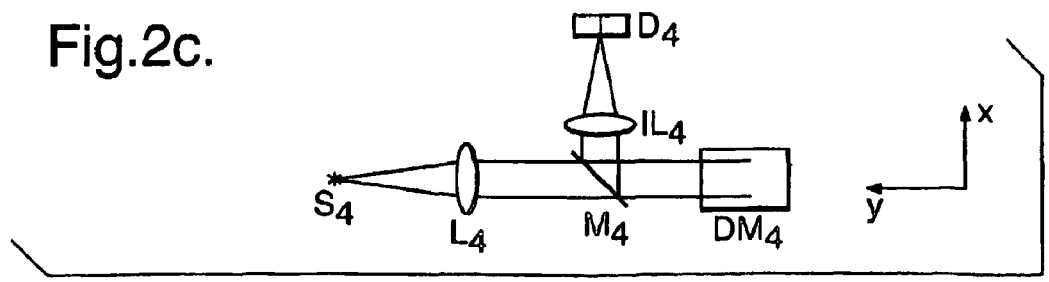
FIG. 2c shows schematically a top view of the ray path of a single beam autofocus system according to an embodiment of the present invention.
Figure 3C:
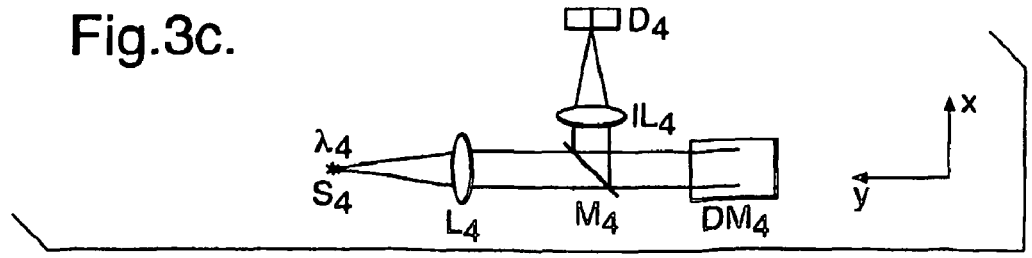
FIG. 3c is a schematic top view of a ray path of the single beam autofocus system according to an embodiment of the present invention.

Embodiments of single-beam autofocus are shown in FIGS. 2C and 3C, where a separate light source, $S_4$ of wavelength $\lambda_4$, and detector $D_4$ are shown. The wavelength $\lambda_4$ is necessarily distinct from the sample fluorescence, and preferentially a wavelength that cannot excite appreciable fluorescence in the sample. Thus, $\lambda_4$ is preferentially in the near infrared, exemplarily 800-1000 nm. The partially transmitting, partially reflecting mirror, $DM_4$, is preferentially dichroic, reflecting $\lambda_4$ and transmitting $\lambda_n$ and $\delta\lambda_n$, n=1, 2, 3. Optically-based autofocus mechanisms suitable for the present application are known. For example, an astigmatic-lens-based system for the generation of a position error signal suitable for servo control is disclosed in *Applied Optics* 23 565-570 (1984). A focus error detection system utilizing a "skew beam" is disclosed in *SPIE* 200 73-78 (1979). The latter approach is readily implemented according to FIGS. 2C and 3C, where $D_4$ is a split detector.

For use with a microtiter plate having a sample residing on the well bottom, the servo loop must, however, be broken to move between wells. This can result in substantial time delays because of the need to refocus each time the illumination is moved to another well.

Figure 4:
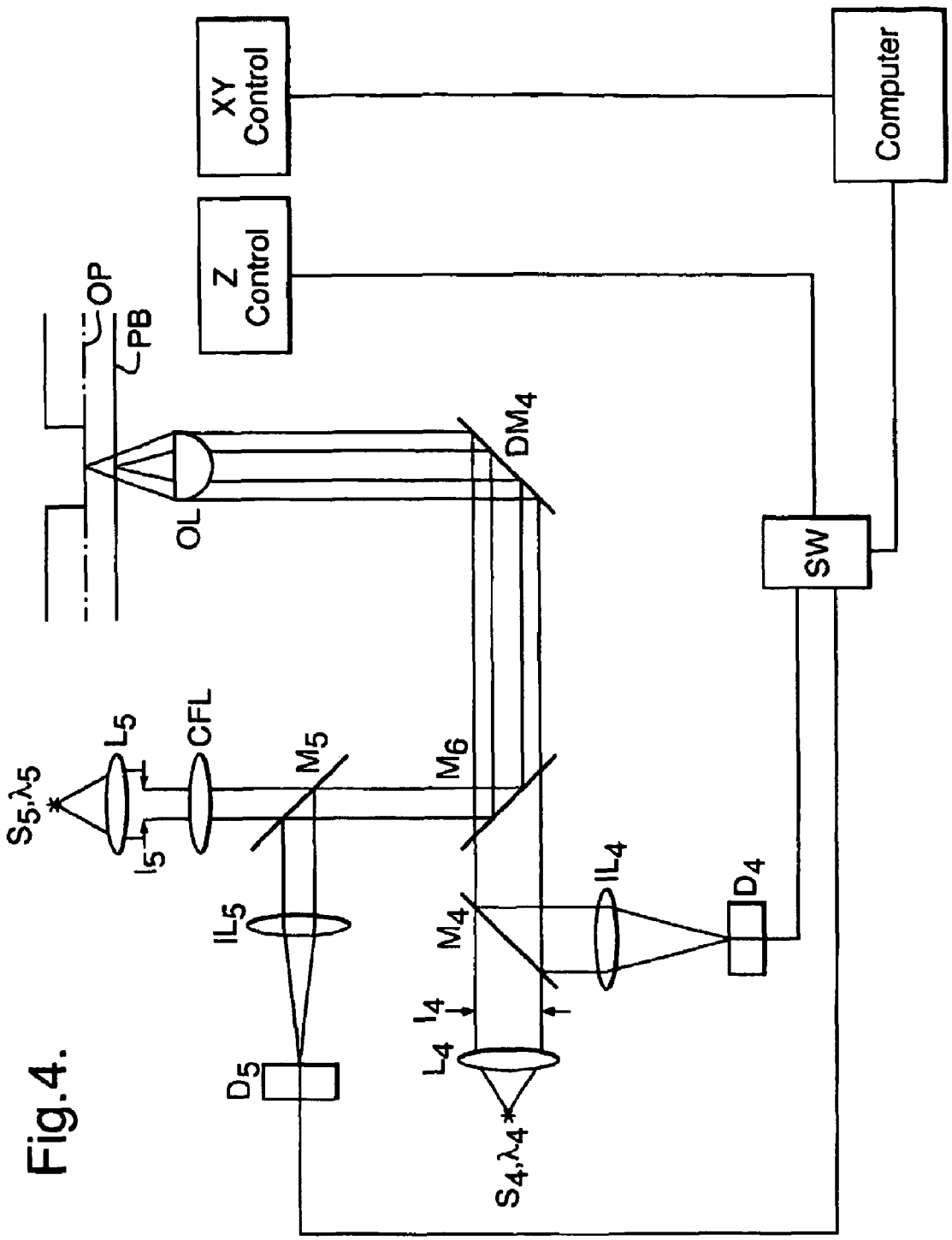
FIG. 4 shows schematically a side view of a two beam autofocus system according to an embodiment of the present invention.

Continuous closed-loop control of the relative position of the sample plane and the object plane is provided in a preferred embodiment of the present invention, depicted in FIG. 4. This system utilizes two independent beams of electromagnetic radiation. One, originating from $S_5$, is focused on the continuous surface, exemplarily the bottom of a microtiter plate. The other, originating from $S_4$, is focused on the discontinuous surface, exemplarily the well bottom of a microtiter plate. In one embodiment, the beams originating from $S_4$ and $S_5$ have wavelengths $\lambda_4$ and $\lambda_5$, respectively. $\lambda_4$ is collimated by $L_4$, apertured by iris $I_4$, and focused onto the discontinuous surface by the objective lens OL. $\lambda_5$ is collimated by $L_5$, apertured by iris $I_5$, and focused onto the continuous surface by the lens CFL in conjunction with the objective lens OL. The reflected light is focused onto the detectors $D_4$ and $D_5$ by the lenses $IL_4$ and $IL_5$, respectively. The partially transmitting, partially reflecting mirror, $DM_4$, is preferentially dichroic, reflecting $\lambda_4$ and $\lambda_5$ and transmitting $\lambda_n$ and $\delta\lambda_n$, n=1, 2, 3. The mirrors, $M_4$, $M_5$ and $M_6$, are partially transmitting, partially reflecting. In the case that $\lambda_4$ and $\lambda_5$ are distinct, $M_6$ is preferentially dichroic.

According to the embodiment wherein the sample resides in a microtiter plate, $\lambda_4$ is focused onto the well bottom. The object plane can be offset from the well bottom by a variable distance. This is accomplished by adjusting $L_4$ or alternatively by an offset adjustment in the servo control loop. For convenience of description, it will be assumed that $\lambda_4$ focuses in the object plane.

The operation of the autofocus system is as follows. If the bottom of the sample well is not in the focal plane of objective lens OL, detector $D_4$ generates an error signal that is supplied through switch SW to the Z control. The Z control controls a motor (not shown) for moving the microtiter plate toward or away from the objective lens. Alternatively, the Z control could move the objective lens. If the bottom PB of the microtiter plate is not at the focal plane of the combination of the lens CFL and the objective lens OL, detector $D_5$ generates an error signal that is applied through switch SW to the Z control. An XY control controls a motor (not shown) for moving the microtiter plate in the object plane OP of lens OL.

As indicated, the entire scan is under computer control. An exemplary scan follows: At the completion of an image in a particular well, the computer operates SW to switch control of the servo mechanism from the error signal generated by $D_4$ to that generated by $D_5$; the computer then directs the XY control to move the plate to the next well, after which the servo is switched back to $D_4$.

The "coarse" focusing mechanism utilizing the signal from the bottom of the plate is used to maintain the position of the sample plane to within the well-to-well variations in the thickness of the plate bottom, so that the range over which the "fine" mechanism is required to search is minimized. If, for example, the diameter of the iris $I_5$ is 2 mm and $IL_5$ is 100 mm, then the image size on the detector will be ~100 µm. Similarly, if the diameter of the iris $I_4$ is 0.5 mm and $IL_4$ is 100 mm, then the image size on the detector will be ~400 µm. The latter is chosen to be less sensitive so as to function as a "coarse" focus.

As with the single-beam embodiment described above, the wavelengths $\lambda_4$ and $\lambda_5$ are necessarily distinct from the sample fluorescence, and preferentially wavelengths that cannot excite appreciable fluorescence in the sample. Thus, $\lambda_4$ and $\lambda_5$ are preferentially in the near infrared, such as 800-1000 nm. In addition, the two wavelengths are preferably distinct, for example $\lambda_4$=830 nm, $\lambda_5$=980 nm.

In an alternative embodiment of two-beam autofocus, $\lambda_4=\lambda_5$ and the two beams may originate from the same source. Preferentially, the two beams are polarized perpendicular to one another and $M_6$ is a polarizing beamsplitter.

Pseudo-closed loop control is provided in the preferred embodiment of single-beam autofocus which operates as follows. At the end of a scan the computer operates SW to switch control to a sample-and-hold device which maintains the Z control output at a constant level while the plate is moved on to the next well after which SW is switched back to $D_4$.

Detection Devices

A detection device is used having manifold, independent detection elements in a plane conjugate to the object plane. As discussed above, line illumination is advantageous principally in applications requiring rapid imaging. The potential speed increase inherent in the parallelism of line illumination as compared to point illumination is, however, only realized if the imaging system is capable of detecting the light emitted from each point of the sample along the illumination line, simultaneously.

It is possible to place a charge-coupled device (CCD), or other camera, at the output of the prior art imaging systems described above (White et al., U.S. Pat. No. 5,452,125 and Brakenhoff and Visscher, *J. Microscopy* 171 17-26 (1993)). The resulting apparatus has three significant disadvantages compared to the present invention. One is the requirement of rescanning the image onto the two-dimensional detector, which adds unnecessary complexity to the apparatus. Another is the requirement of a full two-dimensional detector having sufficient quality over the 1000 pixel×1000 pixel array that typically constitutes the camera. The third disadvantage is the additional time required to read the full image from the two-dimensional device.

To avoid these disadvantages and optimize not only imaging speed, within the constraints of high-sensitivity and low-noise detection, but also throughput, a continuous-read line-camera is used and in a preferred embodiment a rectangular CCD is used as a line-camera. Both embodiments have no dead-time between lines within an image or between images. An additional, advantage is that a larger effective field-of-view is achievable in the stage-scanning embodiment, discussed below.

The properties required of the detection device can be further clarified by considering the following preferred embodiment. The resolution limit of the objective lens is <1 µm, typically ~0.5 µm, and the detector comprises an array of ~1000 independent elements. Resolution, field-of-view (FOV) and image acquisition-rate are not independent variables, necessitating compromise among these performance parameters. In general, the magnification of the optical system is set so as to image as large a FOV as possible without sacrificing resolution. For example, a ~1 mm field-of-view could be imaged onto a 1000-element array at 1-µm pixelation. If the detection elements are 20-µm square, then the system magnification would be set to 20×. Note that this will not result in 1-µm resolution. Pixelation is not equivalent to resolution. If, for example, the inherent resolution limit of the objective lens is 0.5 µm and each 0.5 µm×0.5 µm region in the object plane is mapped onto a pixel, the true resolution of the resulting digital image is not 0.5 µm. To achieve true 0.5-µm resolution, the pixelation would need to correspond to a region ~0.2 µm×0.2 µm in the object plane. In one preferred embodiment, the magnification of the imaging system is set to achieve the true resolution of the optics.

Figure 5A:
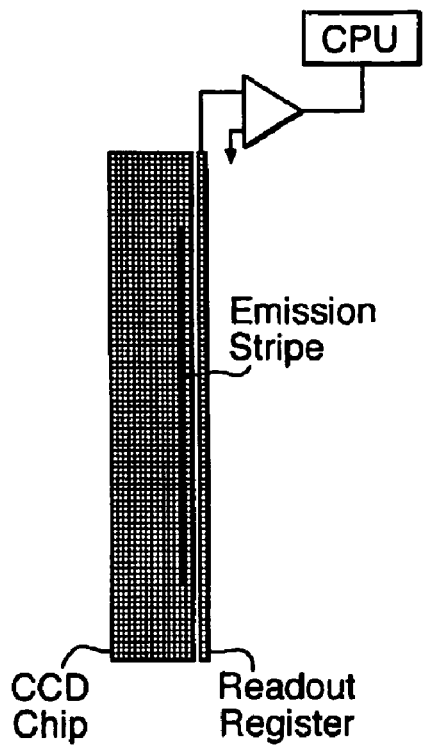
FIGS. 5a, 5b and 5c illustrate schematically a rectangular CCD camera and readout register in accordance with an embodiment of the present invention.
Figure 5B:
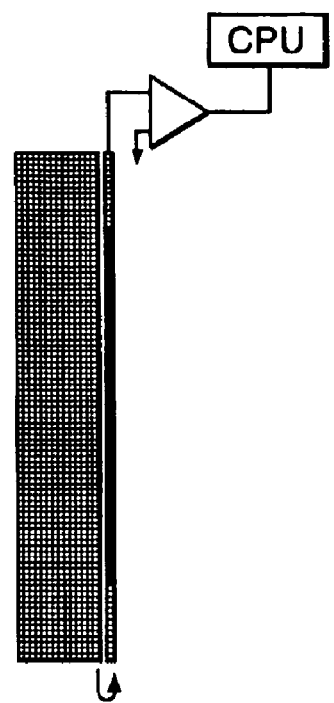
Figure 5C:
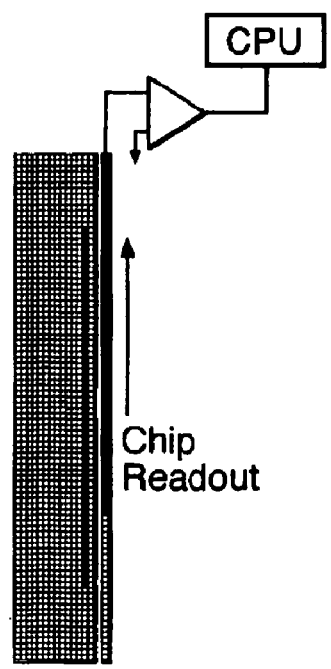

Presently, the highest detection efficiency, lowest noise detection devices having sufficient read-out speed for the present applications are CCD cameras. In FIG. 5, a rectangular CCD camera is depicted having an m×n array of detector elements where m is substantially less than n. The image of the fluorescence emission covers one row that is preferably proximate to the read register. This minimizes transfer time and avoids accumulating spurious counts into the signal from the rows between the illuminated row and the read-register.

In principle, one could set the magnification of the optical system so that the height of the image of the slit $SF_2$ on the CCD camera is one pixel, as depicted in FIG. 5. In practice, it is difficult to maintain perfect alignment between the illumination line and the camera row-axis, and even more difficult to maintain alignment among three cameras and the illumination in the multi-wavelength embodiment as exemplified in FIGS. 2 and 3. By binning together a few of the detector elements, exemplarily two to five, in each column of the camera the alignment condition can be relaxed while suffering a minimum penalty in read-noise or read-time.

An additional advantage of the preferred embodiment having one or more rectangular CCD cameras as detection devices in conjunction with a variable-width detection spatial filter, $SF_2$ in FIGS. 2 and 3 and 210 in FIG. 1, each disposed in a plane conjugate to the object plane, is elucidated by the following. As discussed above, in one embodiment of the present invention the detection spatial filter is omitted and a line-camera is used as a combined detection spatial filter and detection device. But as was also discussed above, a variable-width detection spatial filter permits the optimization of the detection volume so as to optimize the sample-dependent signal-to-noise ratio. The following preferred embodiment retains the advantage of a line-camera, namely speed, and the flexibility of a variable detection volume. The magnification is set so as to image a diffraction-limited line of height h onto one row of the camera. The width of the detection spatial filter d is preferably variable $h \leq d \leq 10\,h$. The detectors in the illuminated columns of the camera are binned, prior to reading, which is an operation that requires a negligible time compared to the exposure- and read-times.

In one preferred embodiment, the cameras are Princeton Instruments NTE/CCD-1340/100-EMD. The read-rate in a preferred embodiment is 1 MHz at a few electrons of read-noise. The pixel format is 1340×100, and the camera can be wired to shift the majority of the rows (80%) away from the region of interest, making the camera effectively 1340×20.

In addition to the above mentioned advantage of a continuous read camera, namely the absence of dead-time between successive acquisitions, an additional advantage is that it permits the acquisition of rectangular images having a length limited only by the extent of the sample. The length is determined by the lesser of the camera width and the extent of the line illumination. In a preferred embodiment the sample is disposed on the bottom of a well in a 96-well microtiter plate, the diameter of which is 7 mm. A strip 1 μm×1 mm is illuminated and the radiation emitted from the illuminated area is imaged onto the detection device. The optical train is designed such that the field-of-view is ~1 mm². According to the present invention, an image of the well-bottom can be generated at 1-μm pixelation over a 1×7-mm field.

Environmental Control

In an embodiment of the present invention, assays are performed on live cells. Live-cell assays frequently require a reasonable approximation to physiological conditions to run properly. Among the important parameters is temperature. It is desirable to incorporate a means to raise and lower the temperature, in particular, to maintain the temperature of the sample at 37° C. In another embodiment, control over relative humidity, and/or $CO_2$ and/or $O_2$ is necessary to maintain the viability of live cells. In addition, controlling humidity to minimize evaporation is important for small sample volumes.

Three embodiments providing a microtiter plate at an elevated temperature, preferably 37° C., compatible with the LCI system follow.

The imaging system preferably resides within a light-proof enclosure. In a first embodiment, the sample plate is maintained at the desired temperature by maintaining the entire interior of the enclosure at that temperature. At 37° C., however, unless elevated humidity is purposefully maintained, evaporation cooling will reduce the sample volume limiting the assay duration.

A second embodiment provides a heated cover for the microwell plate which allows the plate to move under the stationary cover. The cover has a single opening above the well aligned with the optical axis of the microscope. This opening permits dispensing into the active well while maintaining heating and limited circulation to the remainder of the plate. A space between the heated cover plate and microwell plate of approximately 0.5 mm allows free movement of the microwell plate and minimizes evaporation. As the contents of the interrogated well are exposed to ambient conditions though the dispenser opening for at most a few seconds, said contents suffer no significant temperature change during the measurement.

In a third embodiment, a thin, heated sapphire window is used as a plate bottom enclosure. A pattern of resistive heaters along the well separators maintain the window temperature at the desired level.

In additional embodiments, the three disclosed methods can be variously combined.

In an additional preferred embodiment of the invention, employed in automated screening assays, the imaging system is integrated with plate-handling robots, such as the Zymark Twister.

Data Processing System

Figure 6:
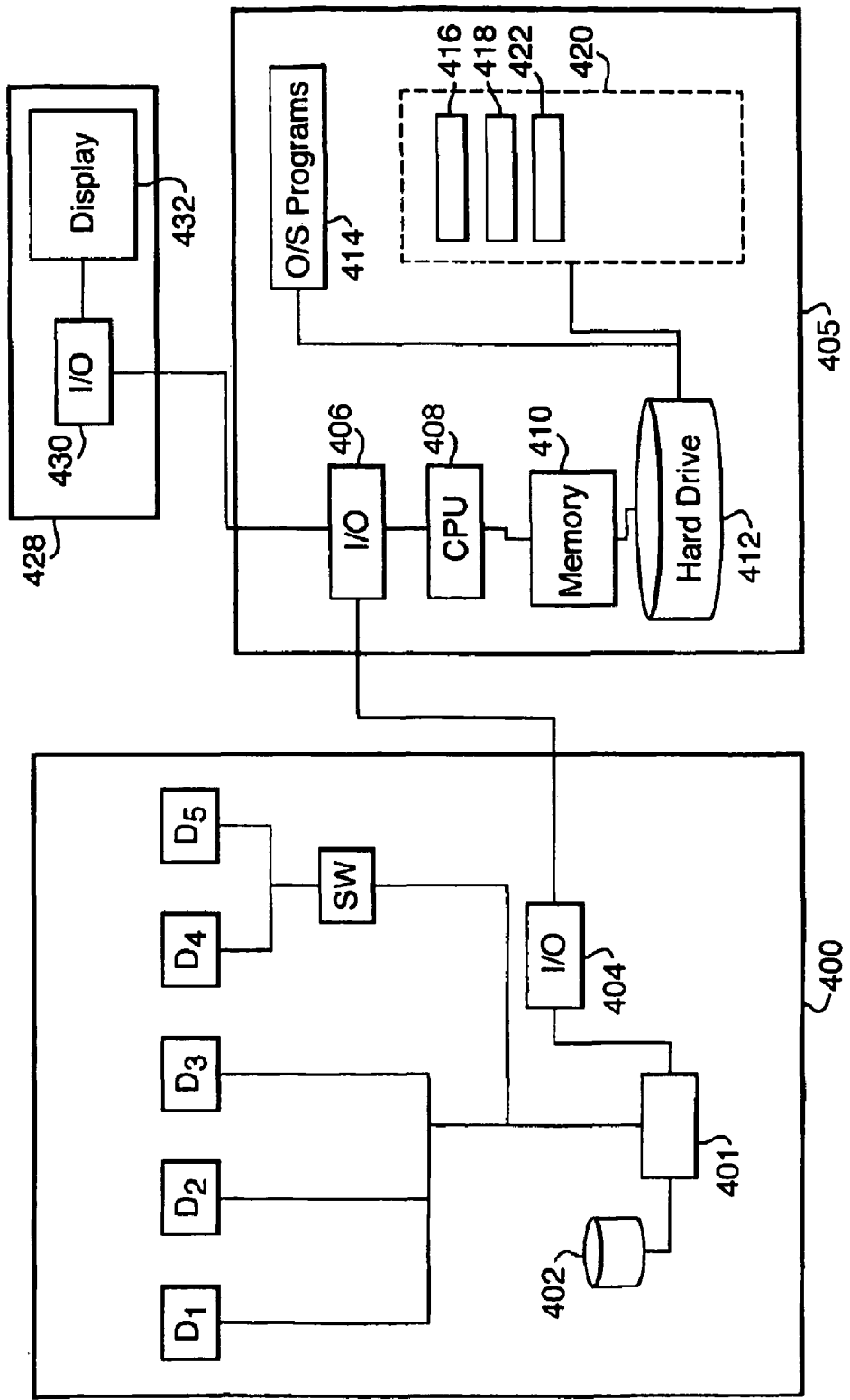
FIG. 6 illustrates schematically data processing components of an imaging data processing system according to an embodiment of the present invention.

FIG. 6 shows a schematic illustration of data processing components of a system arranged in accordance with the invention. The system, based on the Amersham Biosciences IN Cell Analyzer™ system, includes a confocal microscope 400 as described above, which includes the detectors $D_1$, $D_2$, $D_3$, $D_4$, $D_5$, the switch SW, a control unit 401, an image data store 402 and an Input/Output (I/O) device 404. An associated computer terminal 405 includes a central processing unit (CPU) 408, memory 410, a data storage device such as a hard disc drive 412 and I/O devices 406 which facilitate interconnection of the computer with the MDPU and the computer with a display element 432 of a screen 428 via a screen I/O device 430, respectively. Operating system programs 414 are stored on the hard disc drive 412, and control, in a known manner, low level operation of the computer terminal 405. Program files and data 420 are also stored on the hard disc drive 412, and control, in a known manner, outputs to an operator via associated devices and output data stored on the hard disc drive. The associated devices include a display 432 as an element of the screen 428, a pointing device (not shown) and keyboard (not shown), which receive input from, and output information to, the operator via further I/O devices (not shown). Included in the program files 420 stored on the hard drive 412 are an image processing and analysis application 416, an assay control application 418, and a database 422 for storing image data received from the microscope 400 and output files produced during data processing. The image processing and analysis application 416 may be a customized version of known image processing and analysis software packages, such as Image-Pro™ from Media Cybernetics.

The performance of an assay using the confocal microscope 400 is controlled using control application 418, and the image data are acquired. After the end of acquisition of image data for at least one well in a microtiter plate by at least one detector $D_1$, $D_2$, $D_3$, the image data are transmitted to the computer 405 and stored in the database 422 on the computer terminal hard drive 412, at which point data from images can be analysed using the image processing and analysis application 416.

Image Recording and Analysis

Figure 7:
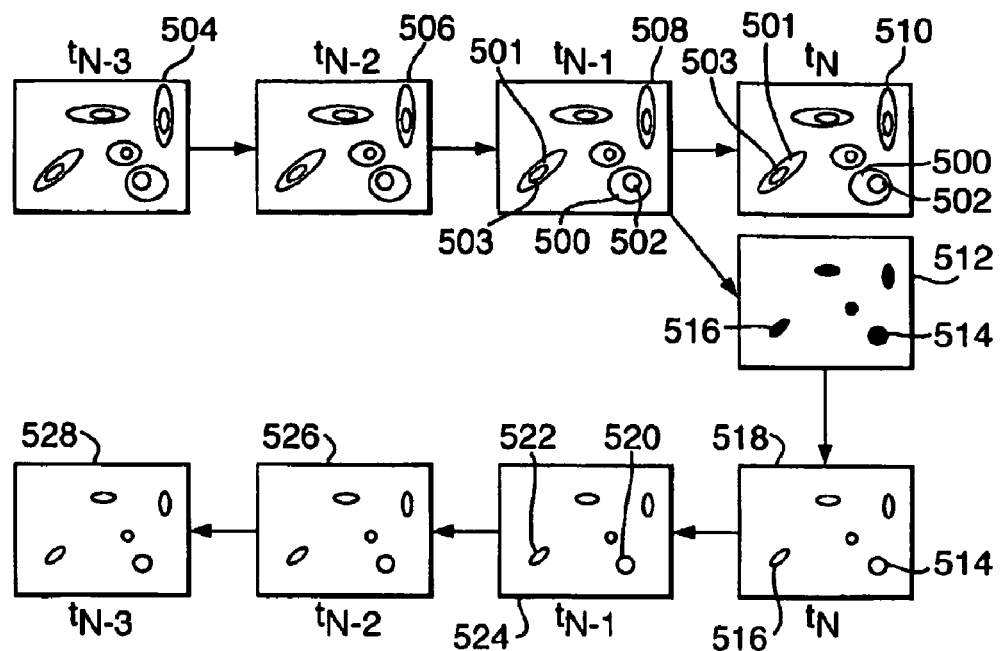
FIG. 7 is a schematic diagram of images and associated spatial definitions of objects within the plurality of biological entities in accordance with an embodiment of the present invention.

FIG. 7 shows a schematic diagram of images of the plurality of biological entities and sets of spatial definitions of objects within the plurality of biological entities.

In this first embodiment of the present invention, the plurality of biological entities is a plurality of biological cells including a first cell 500 and a second, different, cell 501. Within each cell is an object which is a cell nucleus. A first nucleus 502 is contained within the first cell 500 and a second, different, nucleus 503 is contained within the second cell 501. Previous to providing a marker, for example adding a nuclear marker, for the plurality of cells, a series of previous images of a sample of the plurality of cells in one sample well 182 is recorded using the described multi-wavelength configuration of the line-scan confocal imaging system. In this embodiment two independent sets of wavelengths are used in the confocal imaging system and therefore only two sources $S_1$, $S_2$ operating at the two wavelengths $\lambda_1$, $\lambda_2$; two lenses $L_1$, $L_2$; two mirrors $M_1$, $M_2$; two blocking filters $BF_1$, $BF_2$; and two detectors $D_1$, $D_2$ are used. The previous images are recorded using the first source $S_1$, the first lens $L_1$, the first mirror $M_1$, the first blocking filter $BF_1$ and the first detector $D_1$. The first colour channel, including the wavelength $\lambda_1$ at which a fluorescent protein excitation occurs and the wavelength $\delta\lambda_1$ at which the resultant first fluorescence emission occurs, is referred to further as the biological activity colour channel, since images recorded using this channel are to be analysed to produce biological activity data.

The first blocking filter $BF_1$ is a first band pass filter selectively passing a wavelength $\delta\lambda_6$, of the first fluorescence emission. In this embodiment the biological activity colour channel is a green colour channel, detecting fluorescence radiation emitted by a green fluorescent protein (GFP) when excited by the fluorescent protein exciting radiation. The first filter has a maximum transmission at the first emission wavelength $\delta\lambda_1$, of approximately 488 nm. Additionally the first filter has a full width at a half maximum transmission (FWHM), of approximately 50 nm, corresponding to selecting wavelengths of between approximately 740-590 nm (i.e. approximately 565 nm+/−25 nm).

The series of previous images recorded prior to the adding of the marker comprises a third previous image 504 recorded during a fourth previous time period $t_{N-3}$, a second, different, previous image 506 recorded subsequent to the third previous image during a third, different time period $t_{N-2}$ and a first, different, previous image 508 recorded subsequent to the second previous image during a second, different, time period $t_{N-1}$.

A further image is recorded of the plurality of biological cells using the biological activity colour channel. This further image is a subsequent image 510, recorded during a time period $t_N$ subsequent to the adding of the marker.

During the first time period $t_N$ a marked-up image 512 is recorded using the second source $S_2$; the second lens $L_2$; the second mirror $M_2$; the first blocking filter $BF_2$ and the second detector $D_2$. This second colour channel, including the wavelength $\lambda_2$ at which a fluorescent marker excitation occurs and the wavelength $\delta\lambda_2$ at which the resultant second fluorescence emission occurs, is referred to further as the nuclear marker colour channel, since images recorded using this channel are to be analysed to produce spatial definitions relating to the locations at which the nuclear marker is detected in the image.

When the nuclear dye is of the Hoechst type the nuclear marker exciting radiation has a wavelength of approximately 364 nm. For the Hoechst nuclear dye the second blocking filter $BF_2$ is a band pass filter selectively passing the wavelength of the second fluorescence emission $\delta\lambda_2$. The second filter has a maximum transmission at the first emission wavelength $\delta\lambda_2$, of approximately 450 nm. Additionally the filter has a full width at a half maximum transmission (FWHM), of approximately 25 nm, corresponding to selecting wavelengths of between approximately 437.5-462.5 nm (i.e. approximately 450 nm+/−12.5 nm).

When the nuclear dye is of the DRAQ5 type the nuclear marker exciting channel has a wavelength of approximately 633 nm. For the DRAQ5 nuclear dye the second blocking filter $BF_2$ is a band pass filter selecting for a wavelength of the second fluorescence emission $\delta\lambda_2$. At a maximum transmission of the second emission $\delta\lambda_2$ the second band pass filter selects for a wavelength of approximately 695 nm. Additionally the filter has a full width at a half maximum transmission (FWHM), of approximately 55 nm, corresponding to selecting wavelengths of between approximately 667.5-722.5 nm (i.e. approximately 695 nm+/−27.5 nm).

From the marked-up image 512, the data processing system is capable of identifying the cell nuclei including the first and second nucleus 502, 503 using a thresholding process which identifies pixels in which the nuclear marker is present, by virtue of having an intensity above a threshold. Next, nuclei are identified in the form of groups of such thresholded pixels of a given size as above. From this identification of the cell nuclei, a plurality of spatial definitions of the nuclei are detected from the marked-up image 512, including a first spatial definition 514 of the first nucleus 502 and a second, different, spatial definition 516 of the second nucleus 503. A spatial definition includes both a spatial extent, in the form of for example a pixel map, and locational data in the form of, for example an image pixel address of the centroid point of the nucleus.

A subsequent set of spatial definitions 518, comprising substantially all of the spatial definitions of the marked-up image 512, and including the first and the second spatial definition 514, 516, is constructed for the first time period $t_N$. The marked-up image 512 is recorded during the first time period $t_N$ such that the spatial definitions from the marked-up image 512 can be assumed to define spatially the plurality of cell nuclei, including the first nucleus 502 and the second nucleus 503, in the subsequent image 510.

A first previous set of generated spatial definitions 524 is constructed for the second time period $t_{N-1}$ and comprises a plurality of generated spatial definitions for nuclei in the first previous image 508 in which the nuclear marker is less capable of identifying the cell nuclei, including a first generated spatial definition 520 corresponding to the first nucleus 502 and a second, different, generated spatial definition 522 corresponding to the second nucleus 503. Similarly a second previous set 526 and a third previous set 528 of generated spatial definitions are constructed for the time periods $t_{N-2}$ and $t_{N-3}$, respectively.

Figure 8:
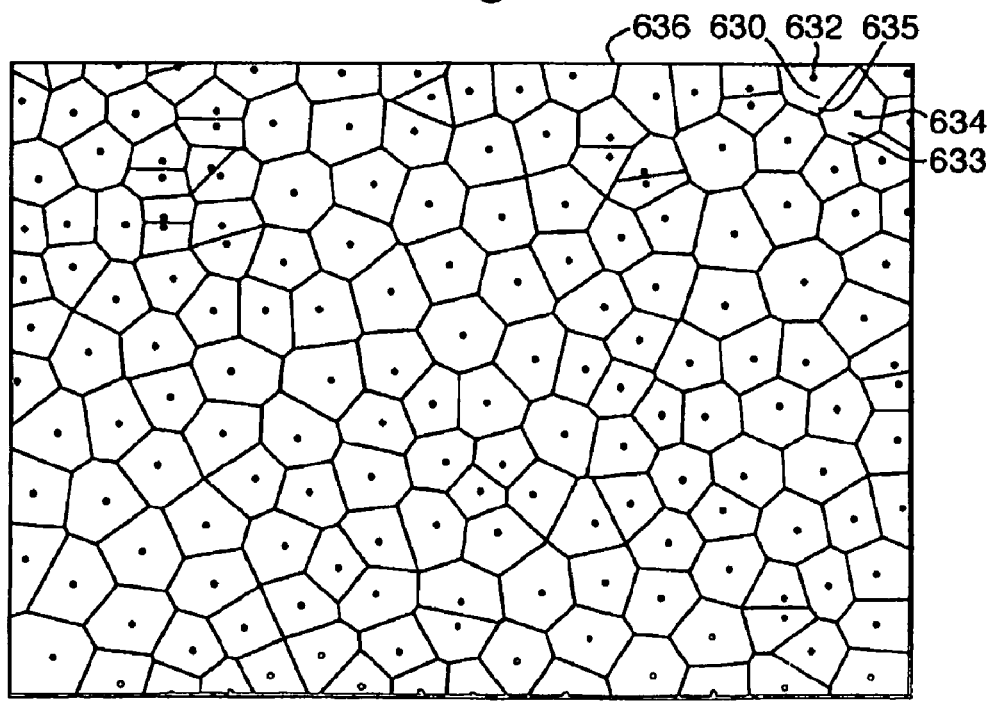
FIG. 8 is a schematic diagram of surrounding spaces of objects of the plurality of biological entities in accordance with an embodiment of the present invention.

FIG. 8 shows schematically spaces surrounding nuclei of the plurality of biological cells.

In this embodiment the surrounding space for each nucleus is a Voronoi region. A first Voronoi region 630 about a first Voronoi centroid point 632 lies adjacent at least one further, different proximate Voronoi region for example a second, different, proximate Voronoi region 633 about a second, different, Voronoi centroid point 634. The first Voronoi region 630 is separated from the at least one further, different proximate Voronoi region, including the second Voronoi region 633, by a boundary 635. The boundary 635 lies at a substantially equal distance between the first Voronoi centroid point 632 and the at least one further, different, proximate Voronoi centroid point. A Voronoi region is determined for each different Voronoi centroid point of the cell nuclei, the resulting plurality of Voronoi regions forming a Voronoi diagram 636. Each different Voronoi centroid point is a centroid point of one different cell nucleus. FIG. 8 is not directly representative of a Voronoi diagram for the plurality of nuclei in the subsequent image 510, but it should be taken for descriptive purposes that the first centroid point and the second centroid point referred to above are the first and the second Voronoi centroid points 632, 634, respectively.

Figure 9:
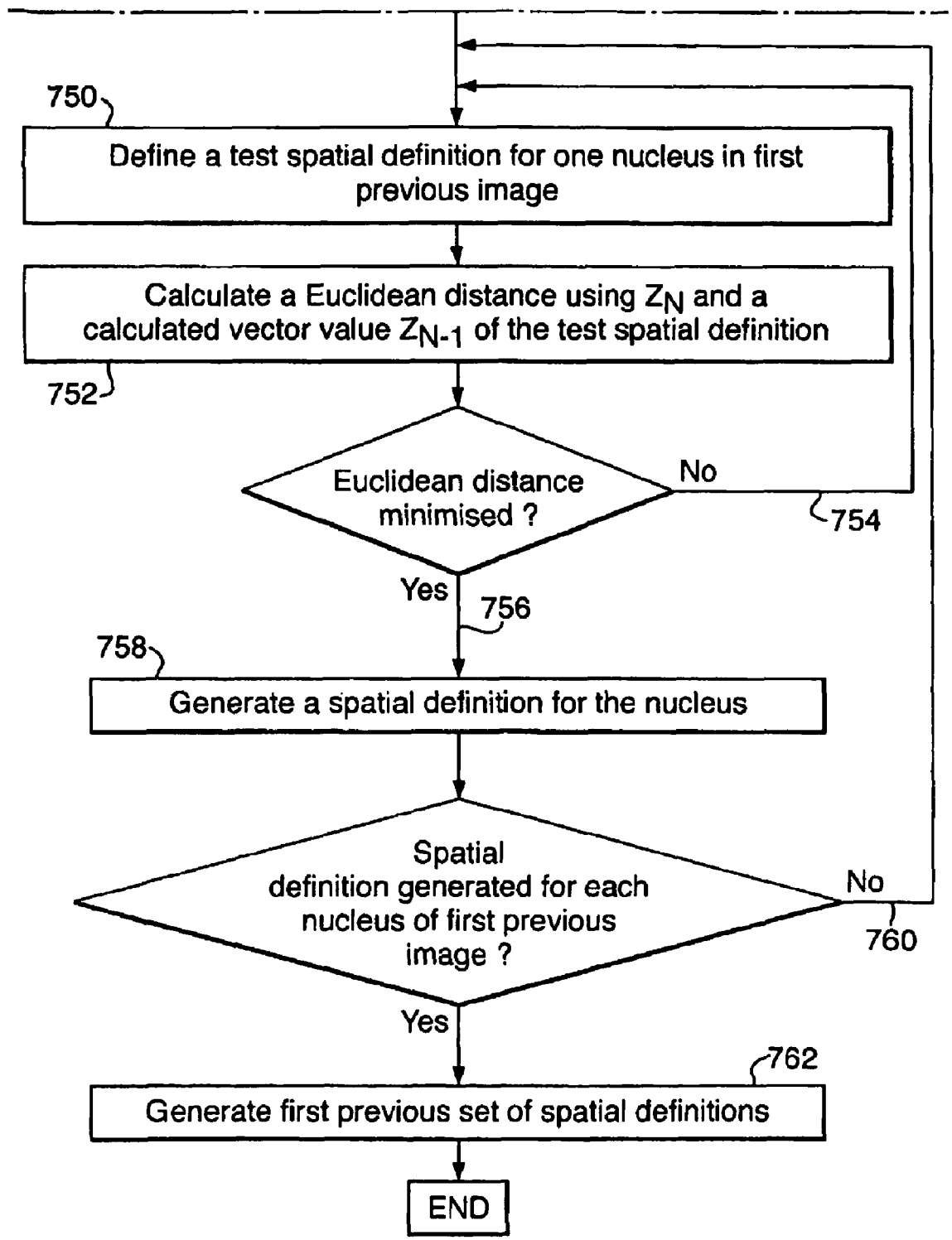
FIG. 9 is a flow diagram showing a method of analysing a plurality of biological entities in accordance with an embodiment of the present invention.

FIG. 9 shows, as a flow diagram, one embodiment of a method of analysing a plurality of biological cells in order to generate spatial definitions for the cell nuclei, in accordance with the present invention.

In a first step 738, the series of previous images of the biological cells, including the first previous image 508, is sequentially recorded. Following this, the nuclear marker is added 740 to the plurality of cells and subsequently a further image is recorded 742 of the plurality of cells using the first colour channel $\lambda_1$ of the confocal imaging system. Using the nuclear marker channel $\lambda_2$ of the confocal imaging system the marked-up image 512 is then recorded 744 during substantially the first time period $t_N$.

The subsequent set of spatial definitions 518 is used to derive data from the subsequent image 510. The derived data comprises at least one value of one or more characteristics of a set i associated with each of the cell nuclei. In this embodiment each value is a vector $Z_N^x$ having K characteristics in the set i. A first nuclear vector $Z_N^1$ is derived 746 from the subsequent image 510 by applying the first spatial definition 514 to the subsequent image 510 and calculating characteristics which apply in the region identified by the spatial definition in the subsequent image 510 for the first nucleus 502. In this embodiment the number K of characteristics in the set i is 2, the characteristics being a mean intensity and a standard deviation. The calculated characteristics in the set i of the first nucleus 502 are then used to construct the first nuclear vector $Z_N^1$.

In a similar manner the second spatial definition 516 is applied to the subsequent image 510 to allow a second nuclear vector $Z_N^2$ to be derived 746 using calculated characteristics in the set i of a region of the subsequent image 510 for the second nucleus 503.

Similarly a nuclear vector $Z_N^x$ for each spatial definition of the set of spatial definitions 518, defining spatially a nucleus of the plurality of cell nuclei in the subsequent image 510, is derived. Each nuclear vector $Z_N^x$ is derived using characteristics in the set i of a region of the subsequent image 510 corresponding to one of the plurality of nuclei.

Next, the Voronoi region for each centroid point of a cell nucleus, as illustrated in FIG. 8, is determined in step 748. In order to determine 748 each Voronoi region, a Voronoi algorithm is used. The Voronoi algorithm defines a boundary about each Voronoi centroid point. For the first and second Voronoi centroid points 632, 634 the Voronoi algorithm defines a portion of the boundary 635 to lie at a substantially equal distance between the first and second Voronoi centroid points 632, 634.

A first test spatial definition (not shown) for the first nucleus 502 is then defined in step 750 within the first Voronoi region 630. The first test spatial definition for the first nucleus 502 has a test spatial extent and test locational data which is the same as the spatial extent and locational data of the first spatial definition 514. Using the first test spatial definition a value of one or more characteristics in the set i of a region for the first nucleus 502 in the first previous image 508 is calculated. In this embodiment the value is a first test vector $Z_{N-1}^{1a}$ a for the first nucleus 502 in the first previous image 508. The first test vector $Z_{N-1}^{1a}$ for the first nucleus 502 has the integer number K of characteristics in the set i which are a mean intensity and a standard deviation.

The first test vector $Z_{N-1}^{1a}$ for the first nucleus 502 is compared with the first nuclear vector $Z_N^1$ by calculating a cost function, which, in this embodiment, involves calculating 752 a first Euclidean distance $E_{N-1}^{1a}$ for the first nucleus 502 using the following relation:

$$E = \sqrt{\sum_{i=1}^{K}(Z_N^1[i] - Z_{N-1}^{1a}[i])^2} \quad (1)$$

Once the first Euclidean distance $E_{N-1}^{1a}$ for the first nucleus 502 has been calculated in step 752 a second, different, test spatial definition (not shown) is determined for the first nucleus 502 in the first previous image 508. The second test spatial definition is determined by selectively removing a perimetric pixel of the test spatial extent of the first test spatial definition and adding the pixel differently to the perimeter of the test spatial extent of the first test spatial definition.

A second, different, test vector $Z_{N-1}^{1b}$ for the first nucleus 502 is then calculated using the second test spatial definition. Similarly to the first test vector $Z_{N-1}^{1a}$ for the first nucleus 502, the second test vector $Z_{N-1}^{1b}$ for the first nucleus 502 includes characteristics in the set i of a region in the first previous image 508.

The second test vector $Z_{N-1}^{1b}$ for the first nucleus 502 is compared with the first nuclear vector $Z_N^1$ by calculating 752 a second, different, Euclidean distance $E_{N-1}^{1b}$ for the first nucleus 502 using relation (1) above.

A plurality of further, different, test spatial definitions (not shown), including a third, different, test spatial definition (not shown), are determined for the first nucleus 502 in the first previous image 508 by differently removing and adding a perimetric pixel of a test spatial extent of the first nucleus 502. When determining a further test spatial definition for the first nucleus 502 in the first previous image 508, the further test spatial definition is determined from a different test spatial definition for the first nucleus 502 already determined and corresponding to a substantially minimum calculated Euclidean distance $E_{N-1}^{1y}$. For example, it is possible that the first Euclidean distance $E_{N-11\alpha}$ for the first nucleus 502 is less than the second Euclidean distance $E_{N-1}^{1b}$ for the first nucleus 502. Therefore, the third test spatial definition is determined from the first test spatial definition of the first nucleus 502 rather than the second test spatial definition of the first nucleus 502. However, if the first Euclidean distance $E_{N-1}^{1a}$ for the first nucleus 502 is greater than the second Euclidean distance $E_{N-1}^{1b}$ for the first nucleus 502, the third spatial definition will instead be determined from the second test spatial definition of the first nucleus 502.

Determining further test spatial definitions for the first nucleus 502 continues iteratively 754 until the calculated Euclidean distance $E_{N-1}^{1y}$ between a further test vector $Z_{N-1}^{1y}$ for the first nucleus 502 and the first nuclear vector $Z_N^1$ is substantially minimised 756. The test spatial definition corresponding to the substantially minimum Euclidean distance $E_{N-1}^{1y}$ for the first nucleus 502 is selected and used to generate 758 the first generated spatial definition 520 of the first nucleus 502 in the first previous image 508.

The substantially minimum Euclidean distance $E_{N-1}^{1y}$ acts as a 'nuclear confidence factor' indicating a level of confidence that a generated spatial definition, in this case the first generated spatial definition 520 of the first nucleus 502, corresponds accurately to the first nucleus 502. For example a minimum Euclidean distance $E_{N-1}^{1y}$ of approximately 0 corresponds to a confidence level of approximately 100%.

Following generation 758 of the first generated spatial definition 520 of the first nucleus in the first previous image 508, a first test spatial definition (not shown) for the second nucleus 503 is defined within the second Voronoi region 633 in a similar manner to that described for generating the first generated spatial definition 520. A first test vector $Z_{N-1}^{2a}$ for the second nucleus 503 is calculated having the characteristics in the set i of a region of the first previous image 508 for the second nucleus 503. The first test vector $Z_{N-1}^{2\alpha}$ for the second nucleus 503 is compared with the second nuclear vector $Z_N^2$ by calculating a first Euclidean distance $E_{N-1}^{2\alpha}$ for the second nucleus 503. Next, a second, different, test spatial definition (not shown) is determined for the second nucleus 503 in the first previous image 508. The second test spatial definition is determined by a method of selectively removing and adding a perimetric pixel of the first test spatial definition as previously described. A second, different, test vector $Z_{N-1}^{2b}$ for the second nucleus 503 is calculated using the second test spatial definition and compared with the second nuclear vector $Z_N^2$ by calculating a second Euclidean distance $E_{N-1}^{2b}$ for the second nucleus 503.

As already similarly described for the first nucleus 503 in the first previous image 508, a plurality of further, different test spatial definitions are determined iteratively for the second nucleus 503 by selectively removing and adding a perimetric pixel of a different test spatial definition of the second nucleus 503 already determined in the first previous image 508. A test spatial definition for the second nucleus 503 in the first previous image 508 is selected and corresponds to a substantially minimum Euclidean distance $E_{N-1}^{2b}$ between the second vector $Z_N^2$ and the selected test spatial definition. This selected test spatial definition is used to generate 758 the second, different, generated spatial definition 522 corresponding to the second nucleus 503. Similarly the substantially minimum Euclidean distance acts as a 'nuclear confidence factor' for the second nucleus.

Similarly to generating the first generated spatial definition 520 and the second generated spatial definition 522, a further, different, generated spatial definition is generated 758 for each nucleus of the first previous image 508 successively 760.

Using the generated spatial definition for each nucleus of the first previous image 508 including the first and second generated spatial definitions, 520, 522 respectively, the first previous set of generated spatial definitions 524 is constructed 762. The first previous set 524 is constructed 762 for substantially the second time period $t_{N-1}$. The first previous set 524 comprises a proportion of the generated spatial definitions of the first previous image 508 which have been filtered according to a quality criterion. In this embodiment the quality criterion is a threshold value for the substantially minimum Euclidean distance $E_{N-1}^{xy}$ corresponding to each generated spatial definition. The threshold value is an acceptable value of the 'nuclear confidence factor' for a generated spatial definition and is determined prior to generation of the spatial definitions for the first previous image 508. For each generated spatial definition, if the substantially minimum Euclidean distance $E_{N-1}^{xy}$ corresponding to a generated spatial definition has a value greater than the determined threshold value, the generated spatial definition has an unacceptable value of the 'nuclear confidence factor' and is not included in the constructed first previous set of spatial definitions 524. If however, the substantially minimum Euclidean distance $E_{N-1}^{xy}$ has a value less than the determined threshold value, the generated spatial definition has an acceptable value of the 'nuclear confidence factor' and is included in the first previous set 524.

An 'image confidence factor' is additionally calculated for each previous set, including the first previous set 524, to indicate a level of confidence that the generated spatial definitions for each nucleus corresponds accurately to the respective nuclei of the plurality of cell. The 'image confidence factor' is calculated for the first previous set 524 by dividing a sum of the minimum Euclidean distance $E_{N-1}^{1y}$ for each nucleus of the first previous set 524 by a total number of cell nuclei in the first previous set 524.

In a similar method to that described for generating spatial definitions for the first previous image 508 using the subsequent set 518 and the subsequent image 510, the second, different, previous set of spatial definitions 526 is constructed using generated spatial definitions which are generated using the first previous set 524 and the first previous image 508, for the plurality of nuclei in the second previous image 506.

The first generated spatial definition for the first nucleus 502 of the second previous set of generated spatial definitions 526 is generated in a similar way to that by which the first generated spatial definition of the first previous set 524 is generated. In generating the first generated spatial definition for the first nucleus 502 a Voronoi region is determined for a centroid point of the first nucleus 502 in the second previous image 506. A plurality of test spatial definitions for the first nucleus 502 are determined in the second previous image 506 and for each test spatial definition a test vector $Z_{N-2}^{1y}$ for a region for the first nucleus 502 in the second previous image 506 is calculated followed by a Euclidean distance $E_{n-2}^{1y}$ for the first nucleus 502. Based on a substantially minimum value of the Euclidean distance $E_{N-2}^{1y}$ for the first nucleus 502, a test spatial definition for the first nucleus 502 in the second previous image 506 is selected and used to generate a first generated spatial definition of the first nucleus 502 in the second previous image 506. According to a similar method to that just described, a plurality of generated spatial definitions for the second previous image 506 are generated. Both a 'nuclear confidence factor' and an 'image confidence factor' may be calculated in a similar manner to that used for the first previous set 524.

By similarly repeating the method for constructing the second previous set of spatial definitions 526, a plurality of previous sets are constructed, including the third, different, previous set of generated spatial definitions 528. Each previous set comprises a plurality of generated spatial definitions for nuclei in a previous image of the biological cells.

Figure 10:
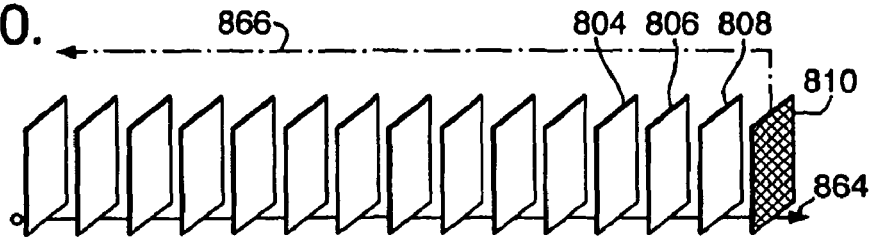
FIGS. 10-13 show schematically temporal directions of analysis of images of biological entities according to different embodiments of the present invention.

FIG. 10 shows schematically a temporal direction of analysis of the series of previous images. For the first embodiment, elements of the previous images already described earlier using different figures are labelled using the same reference numerals incremented by 800. Corresponding features and descriptions of these elements should be taken to apply here also.

FIG. 10 shows the subsequent image 810 recorded during the first time period $t_N$ and the previous images including the first, second and third previous images, 808, 806, 804, respectively. A time axis 864 indicates the time periods $t_{N-x}$, relative to each other, during which the previous images are recorded and the first time period $t_N$ during which the subsequent image 810 is recorded. A reverse direction analysis arrow 866 indicates a reverse direction, relative to the time axis 864, in which the previous sets of spatial definitions are generated for the previous images. The reverse direction analysis arrow 866 shows analysis of the previous images occurring in a reverse direction to an order in which they were recorded along the time axis 864.

Having constructed a plurality of sets of generated spatial definitions, characteristics relating to biological activities of cells in each previous image can be analysed using the corresponding previous generated spatial definitions of the cells. One envisaged example involves performing the method of determining a phase of a biological cell cycle as described in International patent application WO 03/031612, the contents of which are incorporated herein by reference without needing to stain cell nuclei with a nuclear dye, for example Hoechst, over the entire course of the assay.

For example, the second previous image 506 can be analysed using the second set of generated spatial definitions 526 to determine data of the cell cycle of the biological cells during each of the time periods $t_{N-3}$, $t_{N-2}$ and $t_{N-1}$. By analysing a plurality of the previous images using the previous sets of generated spatial definitions, data of the cell cycle of the cells may be determined over the series of time periods during which the previous images of the cells were recorded. Additionally the subsequent set of spatial definitions may be used with the subsequent image of the cells to determine data of the cell cycle during approximately the time period $t_N$.

Figure 11:
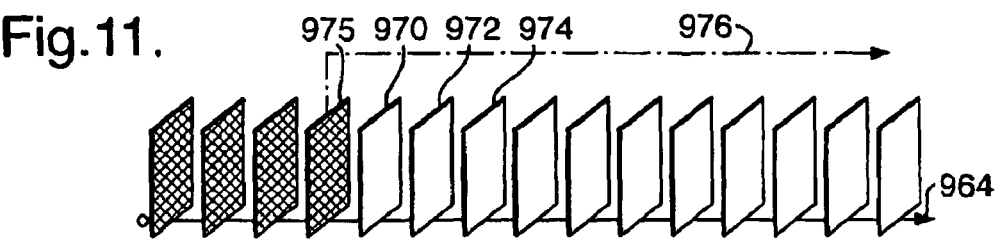

FIG. 11 shows schematically a temporal direction of analysis of a series of images according to a second embodiment of the present invention. The second embodiment is similar to that of the first embodiment in that a marked-up image is recorded during a first time period $t_N$ and the series of images is recorded of a plurality of biological cells. However, the series of images is recorded subsequent to the first time period $t_N$. The series of subsequent images include a first subsequent image 970 recorded during a second time period $t_{N+1}$ a second subsequent image 972 recorded during a third time period $t_{N+2}$ and a third subsequent image 974 recorded during a fourth time period $t_{N+3}$. Additionally a further image 975 of the plurality of biological cells is recorded during the first time period $t_N$. A time axis 964, similarly to the previous embodiment, indicates the time periods $t_{N+x}$, relative to each other during which the subsequent images are recorded. A forward direction analysis arrow 976 indicates a direction in which sets of spatial definitions are generated for the subsequent images, similarly to the first embodiment. In this embodiment the forward direction analysis arrow 976 shows analysis occurring in a forward direction of the subsequent images which corresponds with an order of recording the series of subsequent images along the time axis 964.

In this embodiment, the marker is a cellular marker which, having been provided for the cells, is poorly retained by the cells over a relatively long period of time, and is thus less capable of identifying cell nuclei. Over this relatively long period of time the marker may diffuse out or be actively pumped out of the cell. Alternatively, either the marker may fade due to a photobleaching process, or the marker requires excitation with the use of high intensity ultraviolet radiation during which, if the cells are exposed repeatedly to high intensity ultraviolet radiation over a relatively long period of time, damage to the cells will result.

Figure 12:
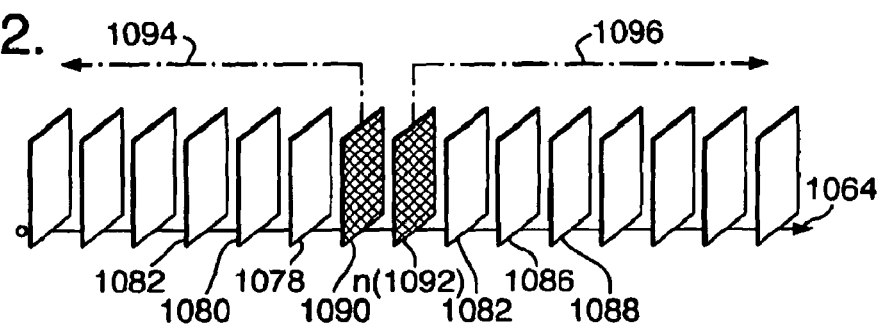

FIG. 12 shows schematically temporal directions of analysis of a series of images according to a third embodiment of the present invention. The third embodiment is similar to previously described embodiments in that a first marked-up image is recorded during a first time period $t_N$ and a series of images is recorded of a plurality of biological cells. Optionally, a second marked-up image is additionally recorded during the first time period $t_N$. A portion of the series of images are recorded previous to the first time period $t_N$ and a portion of the images are recorded subsequent to the first time period $t_N$. The previous images include a first, second and third previous image 1078, 1080, 1082 respectively recorded during a first, second and third previous time period $t_{N-1}$, $t_{N-2}$, $t_{N-3}$ and the subsequent images include a first, second and third subsequent image 1084, 1086 and 1088 respectively recorded during a first, second and third subsequent time period $t_{N+1}$, $t_{N+2}$, $t_{N+3}$. During the first time period $t_N$ a first and an optional second or more further images 1090, 1092, respectively corresponding to the first and second marked-up image, are recorded of the plurality of cells. A time axis 1064 indicates the time periods relative to each other during which the previous and subsequent images are recorded. The first further image 1090 is used to generate spatial definitions for cell nuclei, similarly to previous embodiments, in the previous images in a reverse direction and optionally in a forward direction to an order in which the previous images were recorded, as indicated by a reverse direction first analysis arrow 1094. The second further image is used to generate spatial definitions for cell nuclei in the subsequent images in a forward direction, indicated by a forward direction second analysis arrow 1096, corresponding to an order in which the subsequent images were recorded.

In this embodiment the marker is provided for the cells transiently due to a biological process within the cells which is subject to a temporal modulation. In this example the marker is a temporally-varying signal from a reporter gene of each cell which is expressed during the first time period $t_N$. The reporter gene is a genetic construct system capable of expressing a detectable protein. The reference herein of Naylor L. H. (1999) Biochemical Pharmacology 58, 749-757 describes well known methods of using a variety of reporter genes in mammalian cells. The reporter gene allows a product of the gene to be measurable in the presence of other cellular proteins and is provided for the cell under the control of a chosen regulatory sequence which is responsive to changes in gene expression in a host cell. Such a regulatory sequence is, for example, responsive to hormones, second messengers or other cellular control and signalling factors. The regulatory sequence is appropriately selected such that the reporter gene may be used to assay the effect of, for example, added cellular agents, or cellular processes involving the chosen regulatory sequence. In this example, the reporter gene, when activated, produces an increase in a fluorescence emission signal by activation of a cell permeable substrate. The reporter gene is for example, one of Nitroreductase (described in International Patent Application WO0157237), Beta-lactamase (described in U.S. patent application U.S. Pat. No. 5,741,657) and Green Fluorescent Protein (GFP) (described in U.S. patent application U.S. Pat. No. 6,306,600).

Alternatively in this third embodiment, the marker is for example a Blue Fluorescent Protein for cell nuclei. In order to successfully image this marker it is necessary to fluorescently excite the marker using ultraviolet radiation. Cumulative exposure of the plurality of cells over a relatively long period of time to ultraviolet radiation is toxic to the cells and therefore the marker is only excited in this way during the first time period $t_N$.

Figure 13:
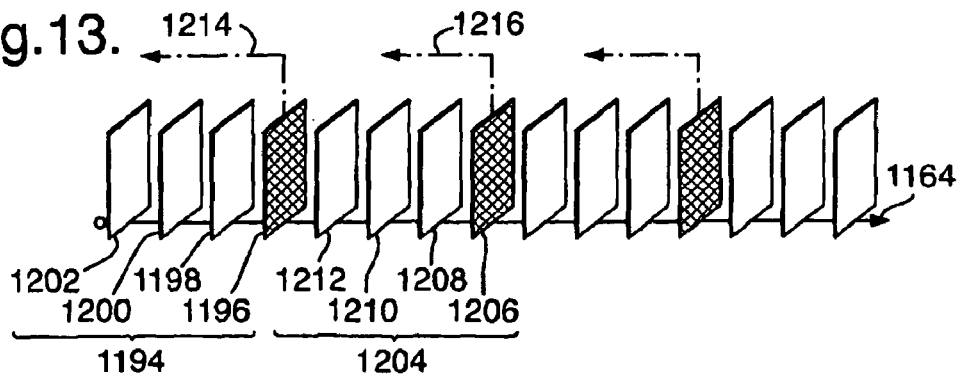

FIG. 13 shows schematically temporal directions of analysis of a series of images in accordance with a fourth embodiment of the present invention. A series of images similar to that of previous embodiments is recorded of the plurality of cells. This plurality of cells is divided into a plurality of sub-series. FIG. 13 shows a first sub-series 1194 comprising a first sub-series further image 1196 recorded during a first sub-series first time period $t_N^1$ and further comprising a first sub-series first, second and third previous image 1198, 1200, 1202 respectively recorded previous to the first time period $t_N^1$ during a first sub-series second, third and fourth time period $t_{N-1}^1$, $t_{N-2}^1$, $t_{N-3}^1$. Additionally a first sub-series marked-up image is recorded during the first sub-series first time period $t_N^1$. A time axis 1164 indicates the time periods, relative to each other, during which the series of images, including the first sub-series 1194 images, were recorded. A reverse direction first sub-series analysis arrow 1214 indicates a direction, being reverse to a direction in time of recording the first sub-series 1194 images, of generating spatial definitions for the cell nuclei in the first sub-series previous images, similarly to previous embodiments, using the first sub-series further image 1196.

A second sub-series 1204 comprises a second sub-series further image 1206 recorded during a second sub-series first time period $t_N^2$ and further comprising second sub-series previous images including a first, second and third previous image 1208, 1210, 1212 respectively recorded previous to the first time period $t_N^2$ during a second sub-series second, third and fourth time period $t_{N-1}^2$, $t_{N-2}^2$, $t_{N-3}^2$.

A reverse direction second sub-series analysis arrow 1216 indicates a reverse direction to an order of recording the second sub-series images, of generating spatial definitions for the cell nuclei in the second sub-series previous images. Each sub-series comprises a further image and three previous images as illustrated in FIG. 13, although it is envisaged that the sub-series comprises more previous images, for example, ten. Further alternatively the previous images may instead be subsequent images, recorded subsequent to a sub-series first period and analysed in a forward direction corresponding to an order of recording the subsequent images. Alternatively still, the images may comprise both previous and subsequent images, spatial definitions for which are generated in both a reverse and a forward direction using the further image.

In all of the embodiments of the present invention described, the marker is capable of identifying cell nuclei. It is further envisaged that the objects of the biological cells may alternatively be other cell objects, for example biological cell mitochondria, biological cell cytoplasm, biological cell lysosomes or bound antibodies and that the marker is capable of identifying the cell mitochondria, cytoplasm, lysosomes or antibodies. It is to be understood that the objects being identified from the recorded images of one embodiment of the present invention are not limited to being of one type, but can include at least two cell objects including for example a cell nucleus, cell mitochondria, cell cytoplasm, cell lysosomes or bound antibodies. Furthermore it is to be understood that alternative nuclear markers to the Hoechst or DRAQ5 type may be used and consequently these alternative markers may be excited by a nuclear marker exciting channel of an appropriate wavelength. Elements, including for example a source $S_n$, a lens $L_n$, a mirror $M_n$, a blocking filter $BF_n$ and a detector $D_n$, of the confocal microscope are suitably adapted for the selected nuclear marker exciting channel and a corresponding nuclear marker channel. When the cell objects include bound antibodies it is envisaged that the biological cells are fixed prior to providing an appropriate marker, for example propidium iodide, for the cells and recording a marked-up image.

It is additionally envisaged that in addition to the use of the marker (primary) capable of identifying cell objects, for example cell nuclei, during a first time period and less capable of identifying cell objects during a second time period, a second marker capable of identifying cell objects during at least the first time period and the second time period is used. This second marker is detected using an appropriate colour channel to record secondary marked-up images of the plurality of cells. Data derived from these secondary marked-up images is used together with data derived from the primary marked-up image, recorded using the primary marker, such that spatial definitions for cell objects in images of the cells may be generated more accurately. Such a second marker may be a fluorescent mitochondrial stain, for example Mito Tracker (Molecular Probes), a fluorescent lysosomal stain, for example LysoTracker (Molecular Probes) or a fluorescent non-specific cellular stain, for example (Cell Tracker (Molecular Probes).

It is further envisaged that the multi-wavelength configuration of the line-scan confocal microscope may be used with more than two independent sets of wavelengths. For example, it is possible that images of biological entities comprising different types of objects, for example cell nuclei and cell mitochondria, are recorded. It is therefore possible that more than two colour channels will be used to record different images of the biological entities to identify differently the different cell objects. A line-scan confocal imaging system having greater than two sources $S_n$, lenses $L_n$, mirrors $M_n$, blocking filters $BF_n$ and detectors $D_n$, for different colour channels may be used.

Spatial definitions according to the described embodiments of the present invention include both a spatial extent about a centroid point and a pixel address of the centroid point. It is further envisaged that spatial definitions may be provided using alternative parameters which spatially define an object within the plurality of biological entities.

The quality criterion described above, in these embodiments being the threshold value, is envisaged as being set by a user and is variable using a trial and error technique. Alternatively, it is envisaged that an automated algorithm may allow the value of the threshold value to be adaptively modified during the course of generating spatial definitions for different previous images. Further alternatively, it is envisaged that the quality criterion is of a different form to a threshold value such that spatial definitions of the objects may be selected.

By selectively removing and adding perimetric pixels of, for example a spatial extent of a spatial definition, it is possible to accommodate a change in a shape of an area of the object, for example the nucleus in the described embodiment. It is additionally envisaged that variation of a spatial definition of an object, for example of a nucleus, over a series of time periods, may be achieved using alternative controlled morphing techniques.

The embodiments of the present invention described comprise recording a series of images of the plurality of biological cells during a series of time periods. Preferably, each sequential time period, for example $t_{N-1}$ and $t_N$, is separated from each other by an equal duration of time. For example it is envisaged that the equal duration in time is approximately between 2 and 20 minutes. It is envisaged, however, that the duration in time may be less than or greater than this. Additionally for example, the series of images comprises approximately up to 60 images ($N \leq 60$) but it is again envisaged that a greater number of images in the series may be recorded. It is alternatively envisaged that different sequential time periods are separated from each other by different, unequal time durations.

In the described embodiments a Voronoi diagram is created which determines a Voronoi region for each nucleus centroid point and which is subsequently used when defining test spatial definitions. It is envisaged that alternative algorithms other than a Voronoi algorithm may be used to determine a surrounding space of the nucleus, or of a centroid point of the nucleus, for use in generating spatial definitions for nuclei in a previous image of the biological cells.

In the above embodiments, the characteristics in the set i are in the form of a mean intensity and a standard deviation of a nucleus in a recorded image of the biological cells. However, alternative or additional characteristics may be calculated for use in generating a spatial definition for an object. These include at least one of a variance, a kurtosis, an auto-correlation function, a spatial correlation measure, a textual correlation measure, a auto correlation function, a fractal dimension, an area, a perimeter, a length of a principle axis, a width of a principle axis, a compactness and an orientation.

When selecting one of the test spatial definitions, a Euclidean distance E is calculated to compare a vector for a nucleus in an image of the biological cells with a test vector of the same nucleus. It is envisaged that at least one of the following functions may alternatively be calculated during selecting a test spatial definition: a cityblock function, a chebyshev distance, a minkowski of order m function, a quadratic function, a Q-positive definite function, a Canberra distance, a non-near distance function, or an angular separation. Additionally, it is foreseen that a test spatial definition may be selected using a combination of at least two of these functions.

It is further envisaged that the 'nuclear confidence factor' and the 'image confidence factor' may be differently calculated, and that the 'nuclear confidence factor' may correspond to cell objects different to cell nuclei.

In further embodiments of the present invention, it is envisaged that, alternative to iteratively defining test spatial definitions and comparing a test vector with a vector of a nucleus, a generated spatial definition is generated by comparing characteristics in a set i of a nucleus in one previous image of the cells with characteristics in a set i of a different previous image of the cells.

In a further embodiment of the present invention, an optimisation algorithm such as a simulated annealing algorithm may be applied to at least some generated spatial definitions. This simulated annealing algorithm may be used to ensure that a selected test spatial definition has been selected using the substantially minimum Euclidean distance E rather than an apparent substantially minimum Euclidean distance E.

In the above embodiments, an image of the biological cells is analysed using a corresponding set of spatial definitions to determine data of a cell cycle of the biological cells during the time period. It is alternatively envisaged that the method of the present invention may be used to detect other parameters of biological cells, for example neurites or granules of fluorescence in the cells.

It is to be understood that any feature described in relation to any one embodiment may be used alone, or in combination with other features described, and may also be used in combination with one or more features of any other embodiments, or any combination of any other embodiments. Furthermore, equivalents and modifications not described above may also be employed without departing from the scope of the invention, which is defined in the accompanying claims.

What is claimed is:

1. A method of analyzing a plurality of biological entities using an imaging apparatus, the method comprising:
   a) acquiring a first image of the biological entities;
   b) adding a marker to said plurality of biological entities after the first image is acquired, said marker being capable of identifying objects within said plurality of biological entities when detected using the imaging apparatus,
   c) recording a marked-up image in which spatial definitions of said objects are identifiable from said marker; and
   d) generating a spatial definition for an object in said first image using data derived from said marked-up image;
   e) acquiring an initial series of images before adding a marker and recording a marked up image, and applying the spatial definition to the initial series of images to enable an operator to evaluate changes in the object over time.

2. The method of claim 1, wherein said marker has a temporally-varying signal.

3. The method of claim 2, wherein said marker is provided by a genetic construct system.

4. The method of claim 1, wherein said generated spatial definition includes at least one of a spatial extent and locational data of the object.

5. The method of claim 1, wherein the generated spatial definition is generated using a spatial definition of the object detected from said marked-up image.

6. The method of claim 1, further comprising:
   e) recording a further image concurrently with the marked-up image; and
   f) deriving spatial definition data from said further image, and analysing said first image using the data derived from the further image.

7. The method of claim 6, wherein said further image is recorded in a first colour channel and said marked-up image is recorded in a second, different colour channel.

8. The method of claim 7, wherein said first image is recorded in said first colour channel.

9. The method of claim 6, further comprising, in step f) deriving data from said further image using data derived from said marked-up image.

10. The method of claim 6, wherein the data derived in step f) comprises a value or values of one or more characteristics associated with the object.

11. The method of claim 10, wherein the one or more characteristics include at least one selected from the group consisting of a mean intensity, a standard deviation, a variance, a kurtosis, an autocorrelation function, a spatial correlation measure, a textual correlation measure, an auto correlation function, a fractal dimension, an area, a perimeter, a length of a principle axis, a width of a principle axis, a compactness and an orientation.

12. The method of claim 1, wherein step d) further comprises:
   i) defining one of a plurality of test spatial definitions;
   ii) calculating a value of one or more characteristics of the first image using the test spatial definition;
   iii) repeating steps i)-ii) for a different one of the plurality of test spatial definitions;
   iv) selecting one of the plurality of test spatial definitions according to the value or values calculated in step ii).

13. The method of claim 12, wherein step iv) further comprises comparing said value calculated in step ii) with a value derived from said further image in step f).

14. The method of claim 13, wherein said comparing comprises calculating a Euclidean distance E, said Euclidean distance E being calculated by the following relation:

$$E = \sqrt{\sum_{i=1}^{K} (Z_N[i] - Z_{N-1}[i])^2}$$

wherein both the value calculated in step ii) and the value derived from said further image in step f) are vectors, respectively $Z_{N-1}$ and $Z_N$, relating to an integer number K of characteristics i.

15. The method of claim 14, wherein step iv) comprises selecting a substantially minimised value of the Euclidean distance E.

16. The method of claim 13, wherein said comparing comprises calculating at least one of a cityblock function, a chebyshev distance, a minkowski of order m function, a quadratic function, a Q-positive definite function, a Canberra distance, a non-near distance function, or an angular separation.

17. The method of claim 1, further comprising repeating step d) to generate a plurality of spatial definitions for a plurality of objects in said first image.

18. The method of claim 17, wherein the plurality of generated spatial definitions are filtered according to a quality criterion.

19. The method of claim 17, wherein step d) further comprises determining a surrounding space of an object detected from said marked-up image, said surrounding space having a boundary separating the surrounding space from at least one different surrounding space of a proximate, different, object and arranging the generated spatial definition to be within the determined surrounding space of the object.

20. The method of claim 19, comprising determining the surrounding space of the object using a Voronoi algorithm.

21. The method of claim 1, further comprising recording a second image of the plurality of biological entities during a third time period and generating a spatial definition for an object in said second image.

22. The method of claim 1, wherein said biological entities are biological cells or cellular components.

23. The method of claim 22, wherein said objects comprise biological cell nuclei.

24. The method of claim 22, wherein said objects comprise biological cell mitochondria, biological cell cytoplasm, biological cell lysosomes or bound antibodies.

25. The method of claim 22, wherein said objects include at least two selected from the group consisting of biological cell nuclei, biological cell mitochondria, biological cell lysosomes, biological cell cytoplasm and bound antibodies.

26. The method of claim 25, wherein when said objects include a bound antibody and said biological cells are fixed prior to said providing of the marker.

27. The method of claim 1, further comprising providing a second, different, marker for said plurality of biological entities, said second marker being additionally used to generate a spatial definition for an object in said first image.

28. The method of claim 27, wherein said second marker is one of a biological cell dye, a biological cell mitochondria dye, a biological cell lysosome dye or a biological cell cytoplasm dye.

29. The method of claim 1, further comprising analysing characteristics of the plurality of biological entities by analysing said first image using said generated spatial definition.

30. A non-transitory computer readable medium for programmed to instruct a computer to analyzing a plurality of biological entities comprising:
   a) acquire a first image of the biological entities, the first image being acquired prior to an introduction of a marker;
   b) add the marker to said plurality of biological entities, said marker being capable of identifying objects within said plurality of biological entities when detected using the imaging apparatus;
   c) record a marked-up image in which spatial definitions of said objects are identifiable from said marker; and
   d) generate a spatial definition for an object in said first image using data derived from said marked-up image;
   e) acquire an initial series of images before adding a marker and recording a marked up image, and applying the spatial definition to the initial series of images to enable an operator to evaluate changes in the object over time.

31. A imaging apparatus for analyzing a plurality of biological entities, said imaging apparatus comprising a computer programmed to:
   acquire an initial series of images of the biological entities, the initial series of images being acquired prior to an introduction of a marker;
   add the marker to said plurality of biological entities, said marker being capable of identifying objects within said plurality of biological entities when detected using the imaging apparatus;
   record a marked-up image, after a marker is introduced to the biological entities, in which spatial definitions of said objects are identifiable from said marker;
   generate a spatial definition for an object in the initial series of images using data derived from said marked-up image; and
   applying the spatial definition to the initial series of images to enable an operator to evaluate changes in the object over time.

* * * * *